(12) United States Patent
Asada et al.

(10) Patent No.: US 11,696,895 B2
(45) Date of Patent: Jul. 11, 2023

(54) FINE PARTICLE COATING (DRUG-CONTAINING HOLLOW PARTICLE AND METHOD FOR MANUFACTURING SAME)

(71) Applicant: Sumitomo Pharma Co., Ltd., Osaka (JP)

(72) Inventors: Takumi Asada, Suita (JP); Mitsuaki Kobiki, Kobe (JP)

(73) Assignee: Sumitomo Pharma Co., Ltd., Osaka (JP)

( * ) Notice: Subject to any disclaimer, the term of this patent is extended or adjusted under 35 U.S.C. 154(b) by 134 days.

(21) Appl. No.: 16/959,017

(22) PCT Filed: Oct. 18, 2018

(86) PCT No.: PCT/JP2018/038895
§ 371 (c)(1),
(2) Date: Jun. 29, 2020

(87) PCT Pub. No.: WO2019/130749
PCT Pub. Date: Jul. 4, 2019

(65) Prior Publication Data
US 2020/0338010 A1    Oct. 29, 2020

(30) Foreign Application Priority Data
Dec. 28, 2017 (JP) .............................. JP2017-254309

(51) Int. Cl.
*A61K 9/50* (2006.01)
(52) U.S. Cl.
CPC ............ *A61K 9/5089* (2013.01); *A61K 9/501* (2013.01); *A61K 9/5015* (2013.01); *A61K 9/5026* (2013.01); *A61K 9/5047* (2013.01)

(58) Field of Classification Search
CPC ..... A61K 9/5089; A61K 9/5047; A61K 9/501
See application file for complete search history.

(56) References Cited

U.S. PATENT DOCUMENTS

| 5,057,323 A | 10/1991 | Niwa et al. |
| 5,087,455 A | 2/1992 | Niwa et al. |

(Continued)

FOREIGN PATENT DOCUMENTS

| EP | 0 640 341 A1 | 3/1995 |
| JP | 7-112932 A | 5/1995 |

(Continued)

OTHER PUBLICATIONS

Yoshihara et al (Design and evaluation of functional hollow granules using two different kinds of polymers, The Academy of Pharmaceutical Science and Technology, Japan, 32nd Annual Meeting) (Year: 2017).*

(Continued)

*Primary Examiner* — Carlos A Azpuru
(74) *Attorney, Agent, or Firm* — Oblon, McClelland, Maier & Neustadt, L.L.P.

(57) ABSTRACT

Provided is a manufacturing method of particles coated with coatable microparticles. The method is a manufacturing method of particles coated with coatable microparticles, comprising the step of adding the coatable microparticles to an inner core comprising a component of interest and a macromolecule, and, while rolling the mixture, coating the mixture while spraying a solvent that can dissolve the macromolecule, wherein the particles coated with the coatable microparticles are coated, component of interest-containing hollow particles.

8 Claims, 10 Drawing Sheets

Appearance of particles in Example 1-1

(56) References Cited

U.S. PATENT DOCUMENTS

| | | |
|---|---|---|
| 2004/0092480 A1 | 5/2004 | Fujinaga et al. |
| 2004/0131679 A1 | 7/2004 | Sugi et al. |
| 2007/0098843 A1 | 5/2007 | Tomohira |
| 2010/0136110 A1 | 6/2010 | Tasaki et al. |
| 2011/0262547 A1 | 10/2011 | Musa et al. |
| 2015/0297520 A1 | 10/2015 | Kobiki et al. |
| 2016/0120813 A1 | 5/2016 | Hayashida et al. |
| 2017/0196815 A1 | 7/2017 | Kobiki et al. |
| 2019/0254976 A1 | 8/2019 | Kobiki et al. |
| 2020/0338010 A1 | 10/2020 | Asada et al. |

FOREIGN PATENT DOCUMENTS

| | | |
|---|---|---|
| JP | 4592590 B2 | 12/2010 |
| JP | 2012-528135 A | 11/2012 |
| JP | 2013-523670 A | 6/2013 |
| JP | 2016-65021 A | 4/2016 |
| WO | WO 00/09133 A1 | 2/2000 |
| WO | WO 02/060448 A1 | 8/2002 |
| WO | WO 2010/038691 A1 | 4/2010 |
| WO | 2014/030656 * | 2/2014 |
| WO | WO 2014/030204 A1 | 2/2014 |
| WO | WO 2014/030656 A1 | 2/2014 |
| WO | WO 2014/181390 A1 | 11/2014 |
| WO | WO 2019/130749 A1 | 7/2019 |
| WO | WO 2019/131891 A1 | 7/2019 |

OTHER PUBLICATIONS

By Leung et al (Enteric coating of micron-size drug particles through a Wurster fluid-bed process, Polymer Technology, 117, 247-252) (Year: 2017).*

Abdul. S., et al., "A flexible technology for modified-release drugs: Multiple-unit pellet system (MUPS)", Journal of Controlled Release, Retrieved from the internet: URL: https://www.sciencedirect.com/science/article/abs/pii/S0168365910003639, 2010, vol. 147, pp. 2-16.

International Search Report dated Nov. 25, 2019 in PCT/JP2019/040923, 3 pages.

Symposium of Particulate Design and Preparations, "Creation and Functional Evaluation of Novel High Content Spherical Hollow Particles" (Oct. 23, 2014), pp. 1-11 (with partial English translation).

2014 AAPS annual meeting and exposition ,"A High-Loading Hollow Spherical Granule, a novel dissolution controllable granule manufacturing technology" (Nov. 2, 2014), 1 page.

The Pharmaceutical Society of Japan, 135th the Annual Meeting, (27R-pm02S), "Application of new hollow particles highly containing a drug to gastric floating preparations" (Mar. 27, 2015), 1 page (with English translation).

The 32th symposium of Particulate Design and Preparations, "Monitoring of the production step of high-content spherical hollow particles through application of PAT", (Oct. 22, 2015), pp. 172-173 (with English translation).

The 13th US-Japan Symposium on Drug Delivery Systems "Basic characteristics and applications of a novel high loading hollow spherical particle" (Dec. 16, 2015), 42 pages.

The Pharmaceutical Society of Japan, 136 the Annual Meeting, (28N-pm03S) "Design and evaluation of hollow particles for sustained release of poorly soluble drug using centrifugal railing granulation method" (Mar. 29, 2016), 1 page.

The Academy of Pharmaceutical Science and Technology, Japan, 30th the Annual Meeting, "Granulation mechanism of spherical hollow particles manufactured by OPUSGRAN technique" (May 19, 2016), 1 page (with English translation).

The 41st Pharmaceutical Drug Discovery Seminar, "Granulation mechanism of spherical hollow particles manufactured by OPUSGRAN technique" (Aug. 25, 2016), 1 page (with English translation).

Japan Society of Pharmaceutical Machinery and Engineering, 26th general meeting, "Application of functional hollow particles to formulation technology", (Oct. 14, 2016) pp. 1-36 (with English translation).

The 33th symposium of Particulate Design and Preparations, "Evaluation of High Content Spherical Hollow Partictes (Opusgran®) as Granules for Tablets", (Oct. 27, 2016), 1 page (with partial English translation).

Formulation and Excipients Research Society, 2nd symposium, "Development of the technique of producing high-content spherical hollow partictes (OPUSGRAN®)—Creation, evaluation of functionality, and PAT application to productions steps-" (Nov. 26, 2016)), 2 pages (with English translation).

Asada, T., et al., "An Innovative method for the preparation of high API-lcaded hollow spherical granules for use in controlled-release formulation", International Journal of Pharmaceutics, vol. 523, 2017, pp. 167-175.

The Pharmaceutical Society of Japan, 137th the Annual Meeting, (25F-am01S) "Using the Box-Behnken experimental design to optimize manufacturing condition of functional hollow granules" (Mar. 24, 2017), 1 page (with English translation).

The Pharmaceutical Society of Japan, 137th the Annual Meeting, (25F-am02S) "Design of functional hollow granules with highly-drug loading using two kinds of polymers" (Mar. 24, 2017), 1 page (with English translation).

The Pharmaceutical Society of Japan, 137th the Annual Meeting, (27PB-pm187) "In-line monitoring of hollow granules(OPUSGRAN®)" (Mar. 24, 2017), 1 page (with English translation).

The 42nd Pharmaceutical Drug Discovery Seminar, "Influence of Manufacturing Conditions of Spherical Hollow Particles with High Drug Content on Internal Structure and Physical Properties of Formulation" (Aug. 24, 2017), 1 page (with English translation).

Japan Society of Pharmaceutical Machinery and Engineering, vol. 26 No. 3 (2017)(238-244) Development of high drug content spherical hollow particle production technology (OPUSGRAN®) (Sep. 5, 2017) , 1 page (with English abstract).

The 51st Lecture and Discussion on Powder Engineering, "Smart Particle Design for high-performance formulations—Creation and Evaluation of Opusgran®-" (Sep. 13, 2017), 42 pages (with English translation).

Asada, T., "Granulation Mechanism of OPUSGRAN®—Technology", Sep. 2017, Phar Tech., Japan, vol. 33, No. 11 (2017), pp. 245-250 with English abstract.

Kuriyama, A., et al., "In-line monitoring of a high shear granulation process using the baseline shift of near infrared spectra" (Oct. 2, 2017), AAPS PharmSciTech.Feb. 2018;19(2):710-718.

The 34th symposium of Particulate Design and Preparations, "Production of High Content Spherical Hollow Particles Using an Intensive Mixer and Evaluation of Their Granule Characteristics" (Oct. 26, 2017), pp. 210-211 (with English translation).

The 34th symposium of Particulate Design and Preparations, "Monitoring of the production step of high-content spherical hollow partides through application of PAT" (Oct. 26, 2017), pp. 210-211 (with English translation).

Asada, T., "Formulation of a poorly water-soluble drug in sustained-release hollow granules with a high viscosity water-soluble polymer using a fluidized bed rotor granulator" (Feb. 27, 2018) International Journal of Pharmaceutics 541 (2018) 246-252.

Asada, T., "Mechanism of the formation of hollow spherical granules using a high shear granulator" (Mar. 7, 2018), European Journal of Pharmaceutical Sciences, vol. 117, 2018, pp. 371-378.

Ochiai, Y., "Smart Particle Design for Advanced Functional Formulations—Creation and Evaluation of Opusgran®—" (Mar. 24, 2018), The Micromeritics. No. 61, 2018, pp. 28-34 (with English translation).

The Pharmaceutical Society of Japan, 138th the Annual Meeting, (27W-pm11) "Preparation and evaluation of hollow spherical granules using granulated polymer" (Mar. 25, 2018), 1 page (with English translation).

Japan Society of Pharmaceutical Machinery and Engineering, 28th general meeting, "Next Generation OPUSGRAN®" (Oct. 18, 2018), 55 pages (with English translation).

Ths 35th symposium of Particulate Design and Preparations, "a granulation management method for high-content spherical hollow particles (OPUSGRAN®) using the latest PAT tool" (Oct. 25, 2018)), 1 page (with partial English translation).

(56) References Cited

OTHER PUBLICATIONS

Ito, O., et al., "Development of amorphous solid dispersion using hollow spherical granules manufacturing technology" (May 16, 2019), The Academy of Pharmaceutical Science and Technology, Japan, 34th the Annual Meeting, 1 page (with English translation).
The 17th Technical Conference, "Method for controlling the end point of granulation of spherical particles using a new PAT tool" (Jul. 17, 2019), 48 pages (with English translation).
Sumitomo Chemical Journal, No. 2019, "DSP original technology Microspherical particle with highty-drug loading (OPUSGRAN®)—Breakthrough technology that overturns existing formulation development methods-" (2019), pp. 67-71 (with partial English translation).
University of Shizuoka, thesis, "Development of Hollow Spherical Granule Granulation Technology and its Application to High-Concentration Controlled-Release Drug Products" (Aug. 1, 2018), 95 pages (with partial English translation).
The Academy of Pharmaceutical Science and Technology, Japan, 29th the Annual Meeting, "Preparation of high-content spherical hollow particles using an agitating granulation method" (May 20, 2014), 2 pages (with English translation).
The Academy of Pharmaceutical Science and Technology, Japan, 32th the Annual Meeting, "Design and evaluation of functional hollow granules using two different kinds of polymers" (May 11, 2017), 2 pages (with English translation).
The 44th Pharmaceutical Drug Discovery Seminar, "Innovation brought about by formulation technology" (Aug. 22, 2019), pp. 1-24 (with English translation).
Extended European Search Report dated Aug. 5, 2021 in European Patent Application No. 18896927.3, 10 pages.
Anonymous, Handbook of Pharmaceutical Excipients, Sixth Edition, 2009, pp. 189-190 with cover page.
International Search Report dated Dec. 4, 2018 in PCT/JP2018/038895 filed on Oct. 18, 2018, 3 pages.
Leung et al., "Enteric coating of micron-size drug particles through a Wuerster fluid-bed process", Powder Technology, 2017, vol. 317, pp. 247-252, ISSN: 0032-5910.
Natsuyama, "Technical development of composite-type fluid-bed processor for fine granulation and fine particle coating-SFP (Super Fine Processor)", Pharm Tech Japan, 2008, vol. 24, No. 4, pp. 153-158, ISSN: 0910-4739 (with English Abstract).
Abdul et al., "A flexible technology for modified-release drugs: Multiple-unit pellet system (MUPS)", Journal of Controlled Release, 2010, vol. 147, 15 total pages.

\* cited by examiner

Fig. 1  Appearance of nuclear particles in Comparative Example 1
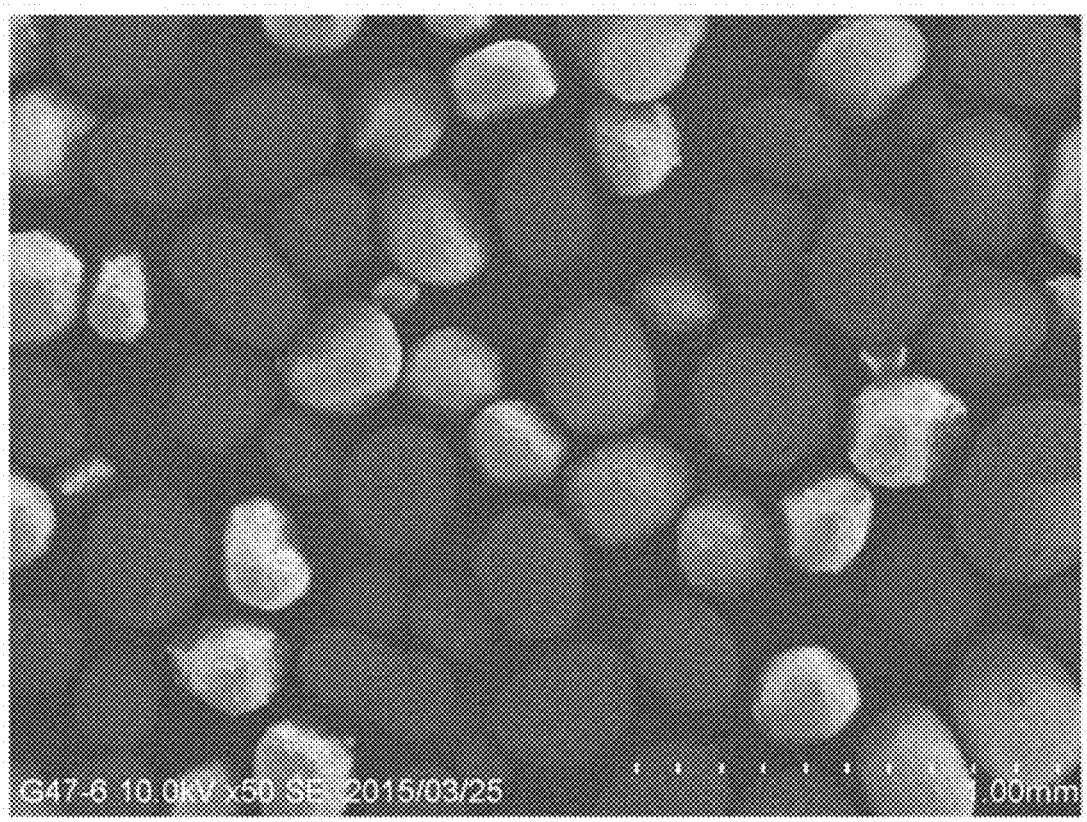
Fig. 2  Appearance of particles in Example 1-1
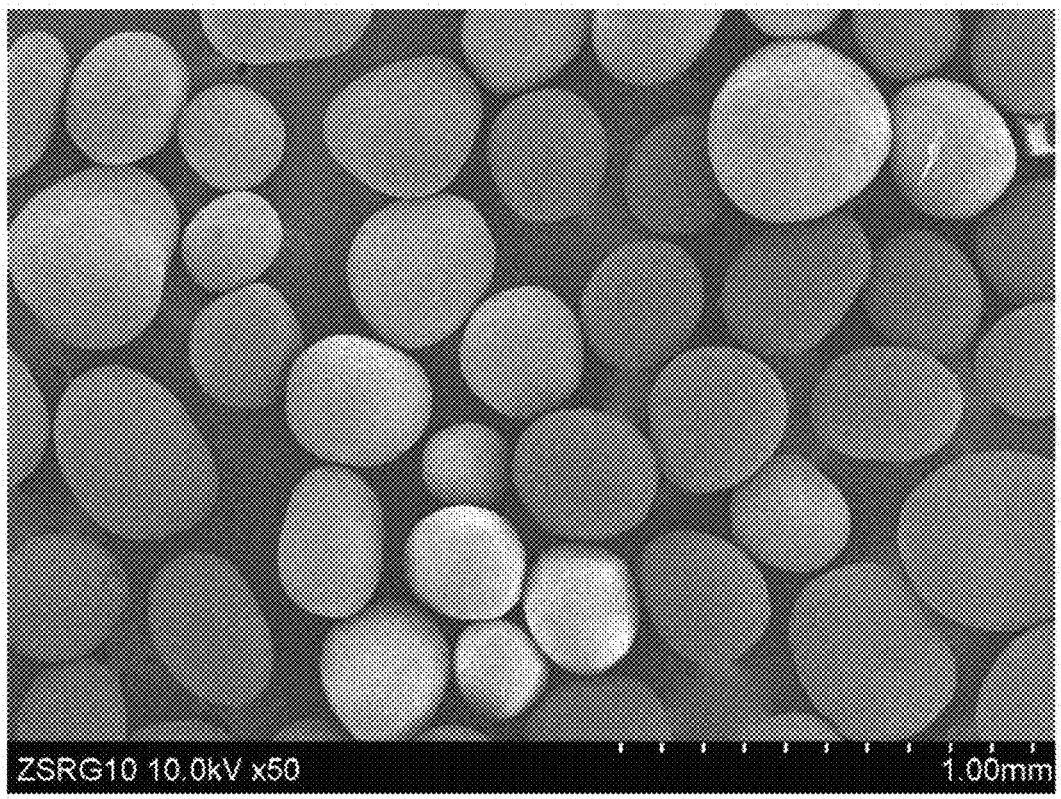

Fig. 3 Results of dissolution tests in Comparative Example 2, Examples 2-1, 2-2, and 2-3
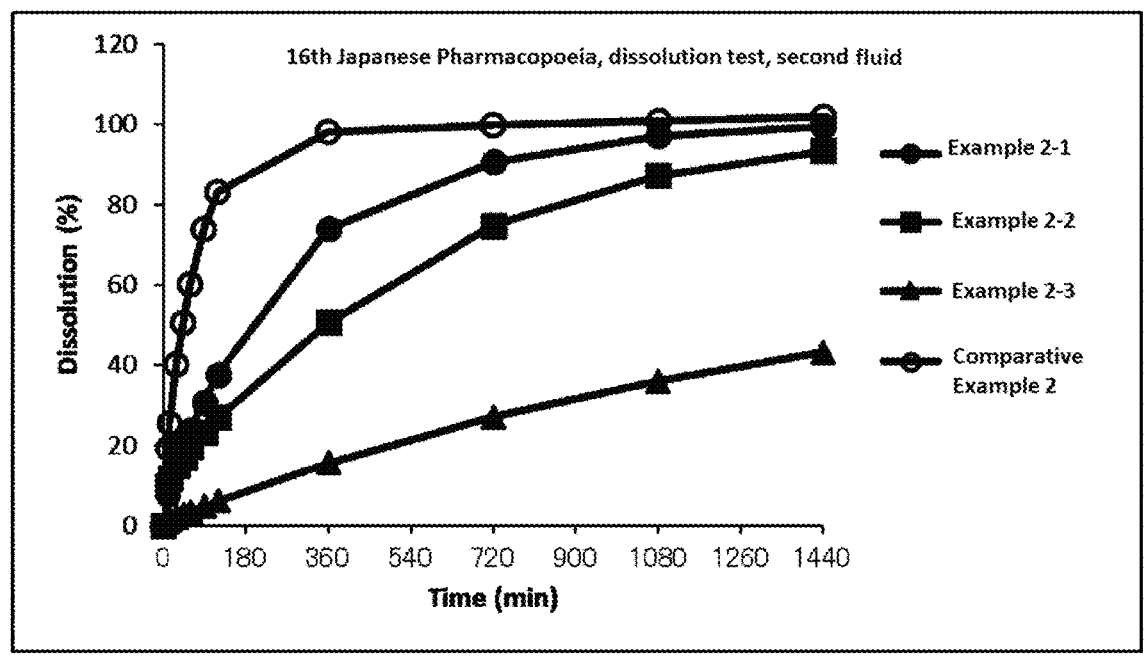
Fig. 4
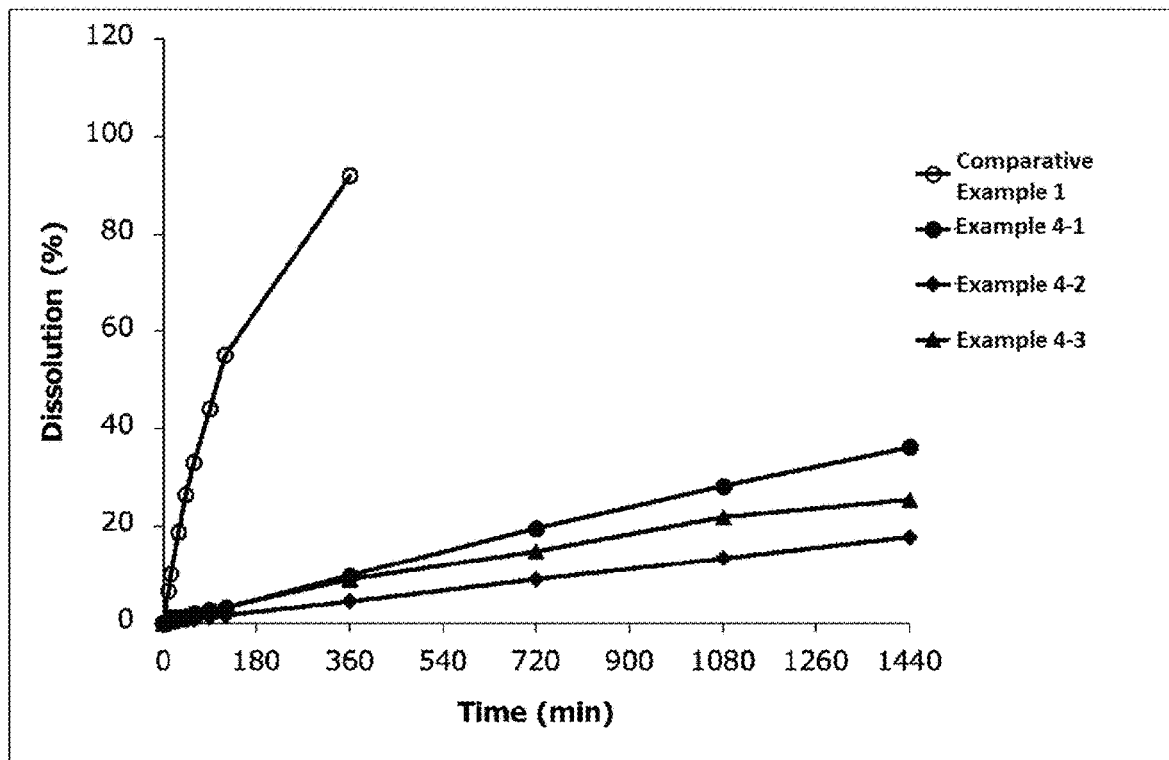

Fig. 5 Results of dissolution tests in Examples 5-1 to 5-5
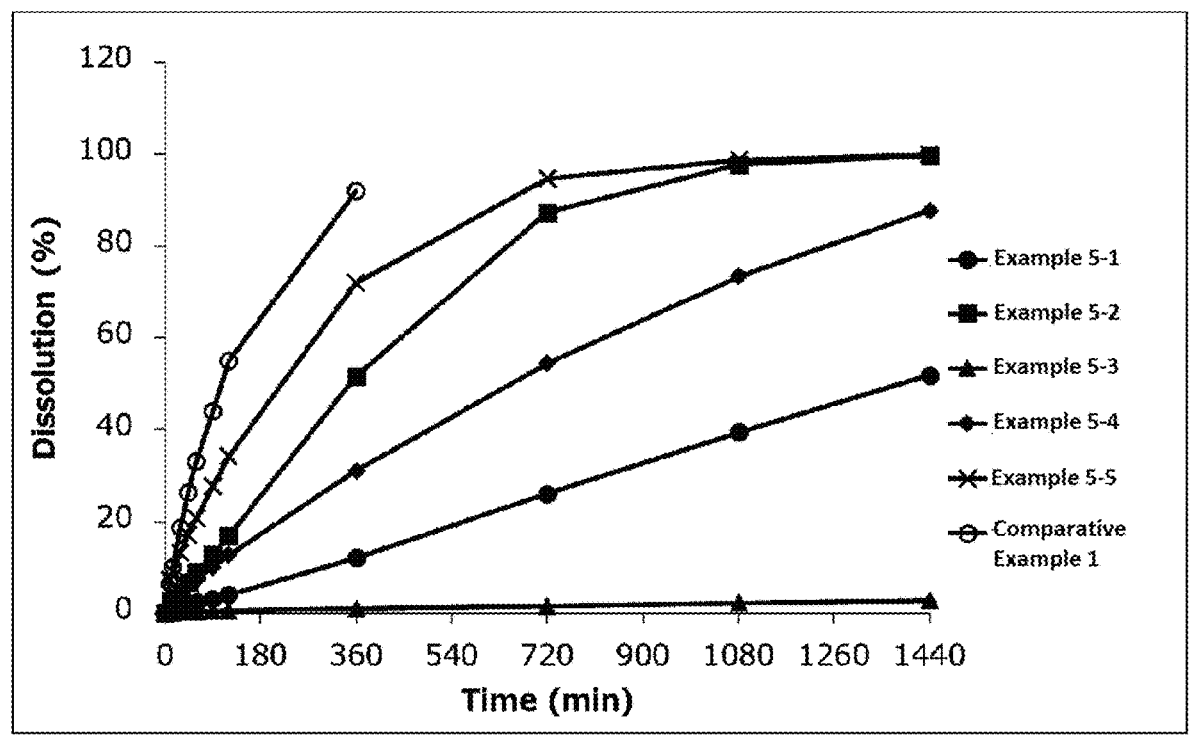
Fig. 6 Stomach soluble macromolecule, Japanese Pharmacopoeia, Dissolution test, first fluid
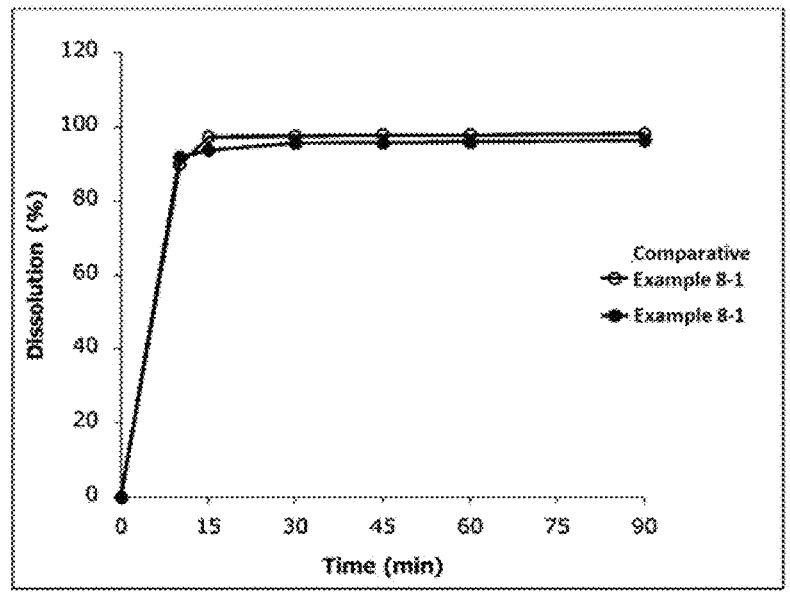

Fig. 7 Stomach soluble macromolecule, Japanese Pharmacopoeia, Dissolution test, Second fluid
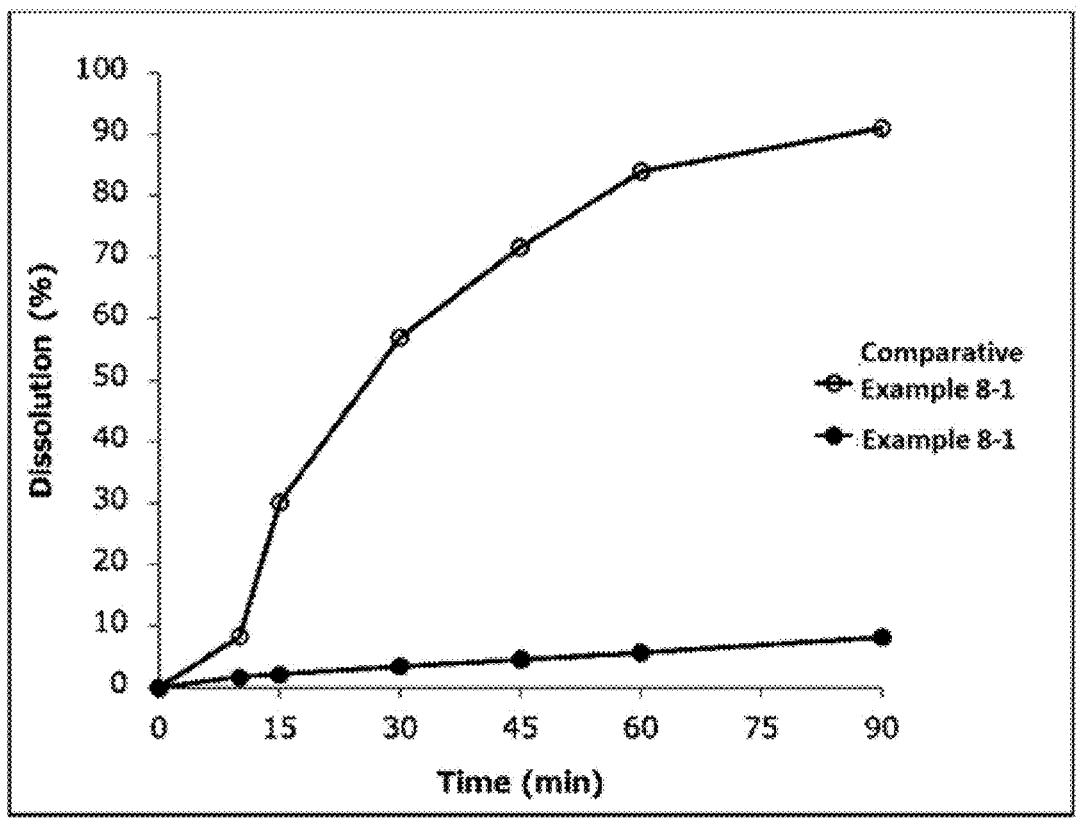
Fig. 8 Enteric macromolecule, Japanese Pharmacopoeia, Dissolution test, first fluid
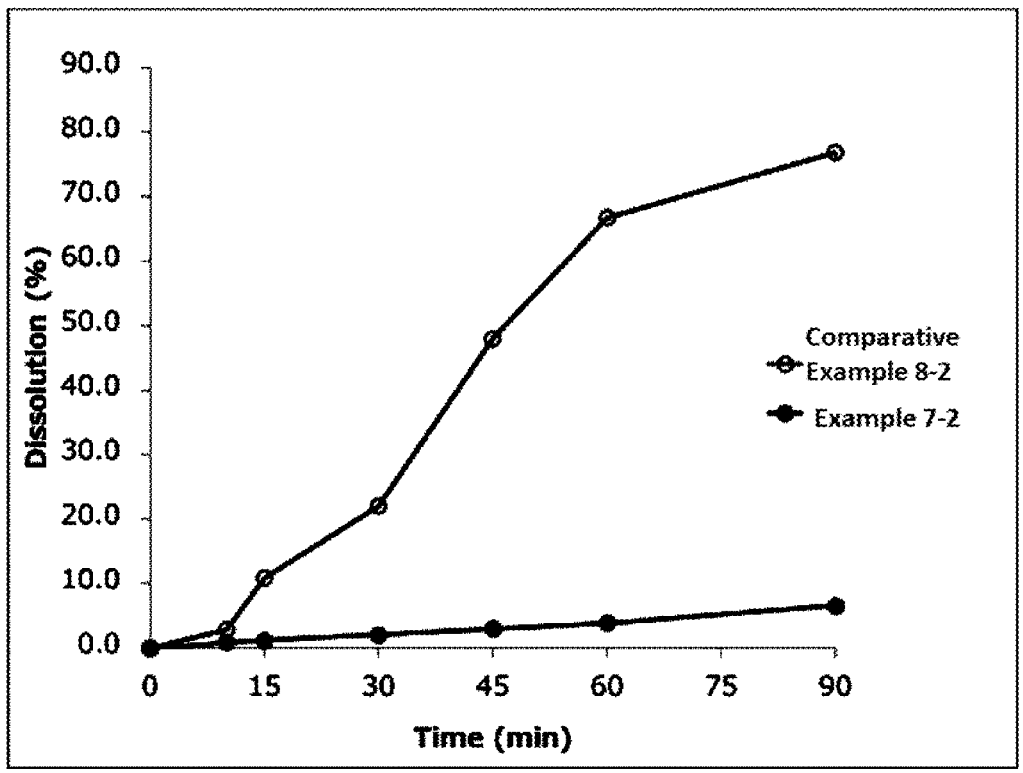

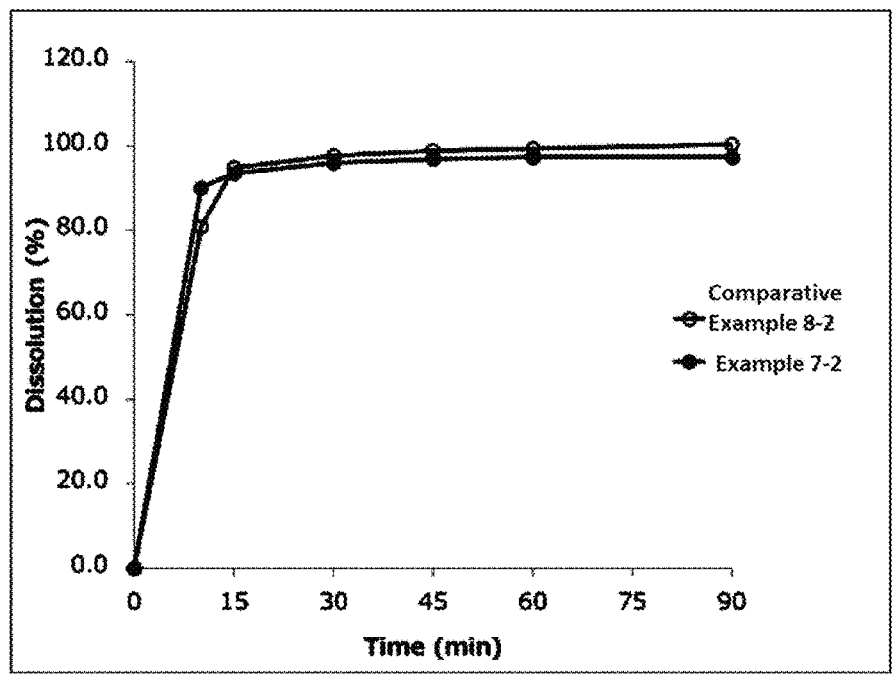
Fig. 9 Enteric macromolecule, Japanese Pharmacopoeia, Dissolution test, second fluid
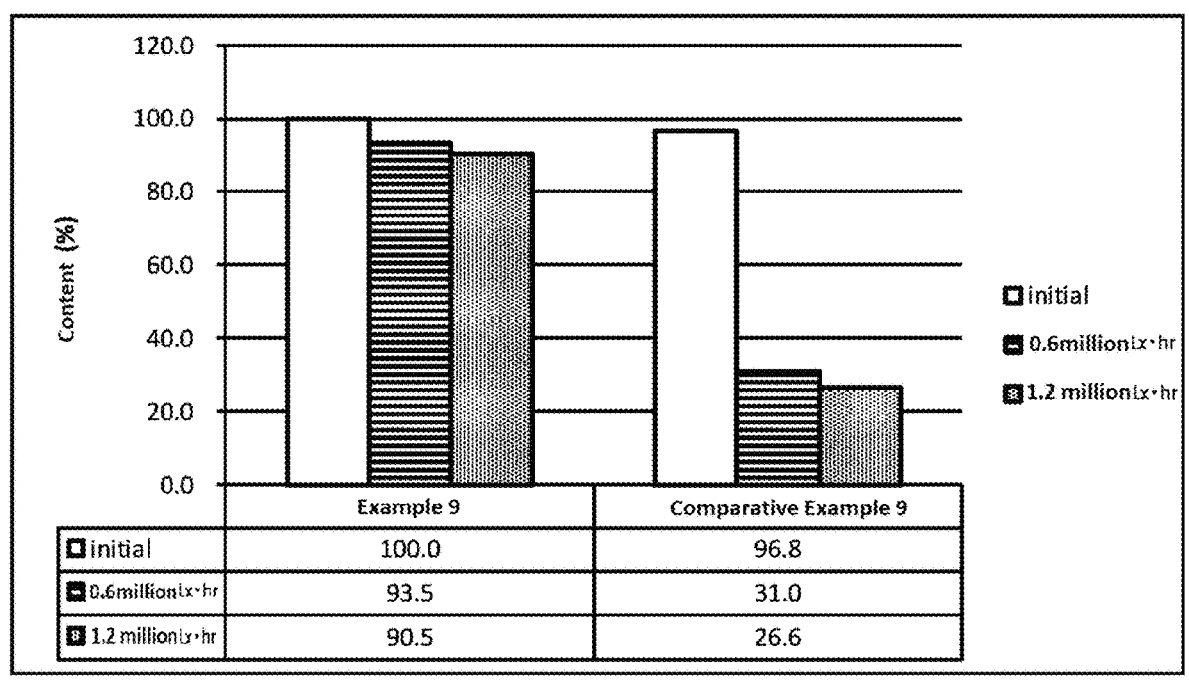
Fig. 10

Fig. 11
Particles containing multiple active pharmaceutical ingredients
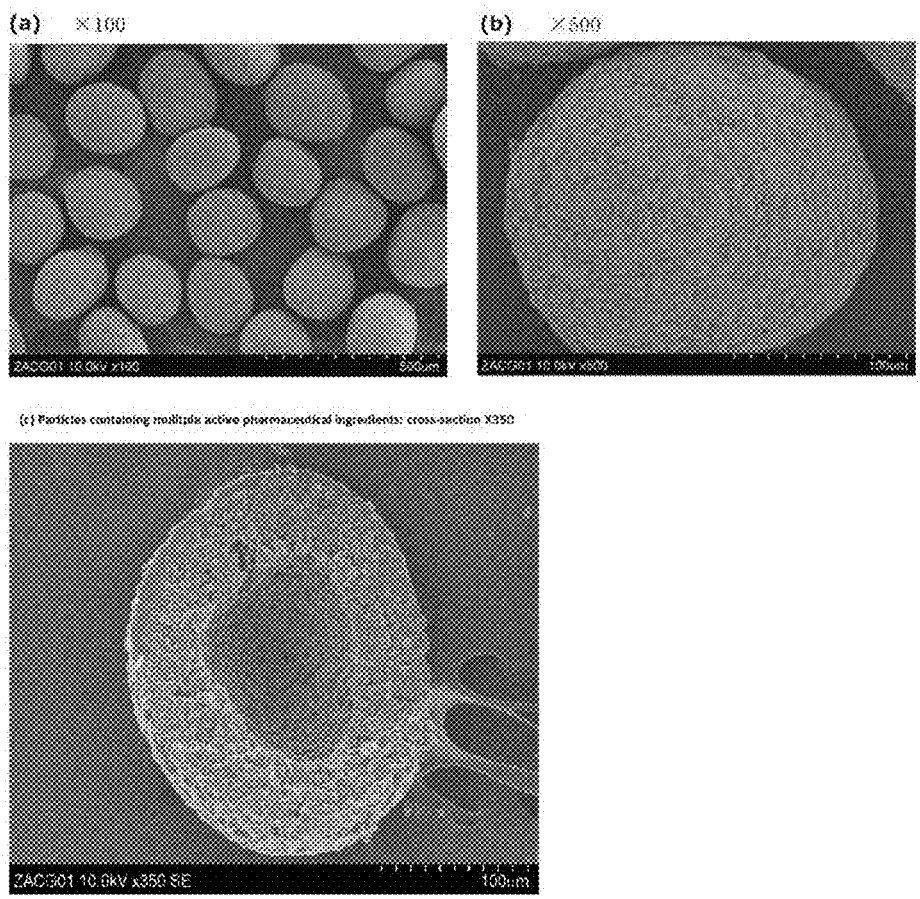
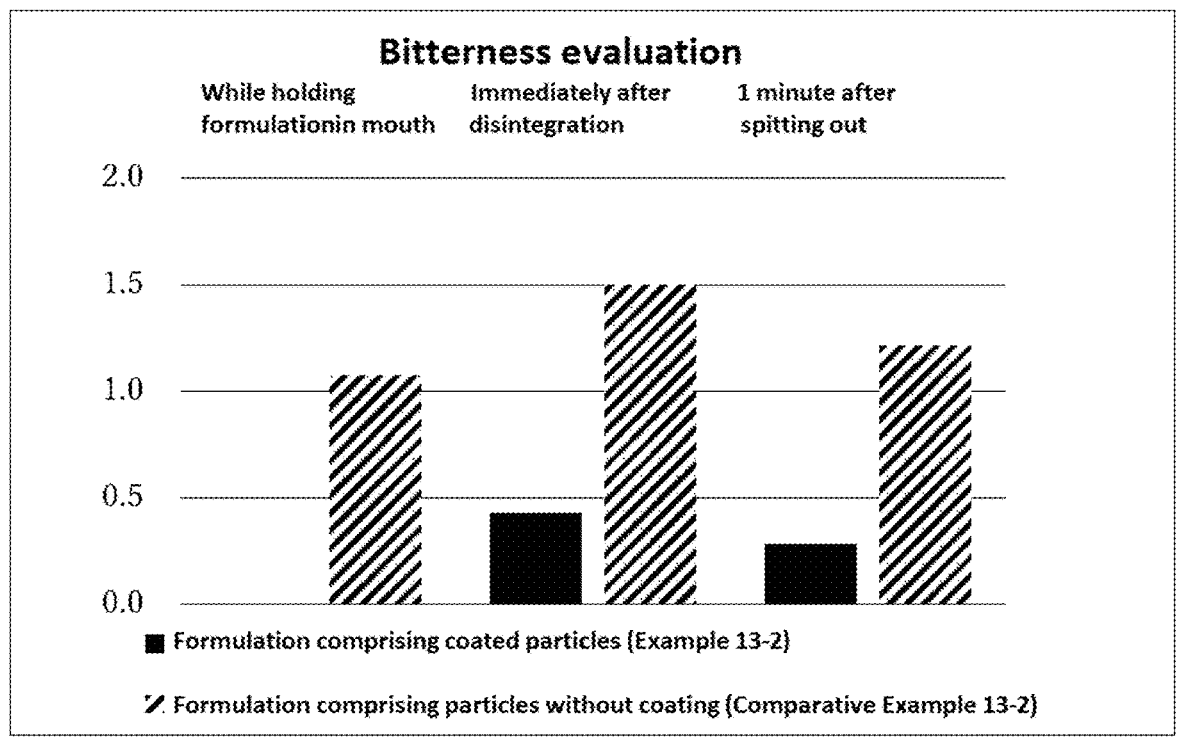
Fig. 12. Results of sensory evaluation test Fig.17
Results of Raman imaging on partial cross section of particles in Example 1-3
(a) CCD camera image
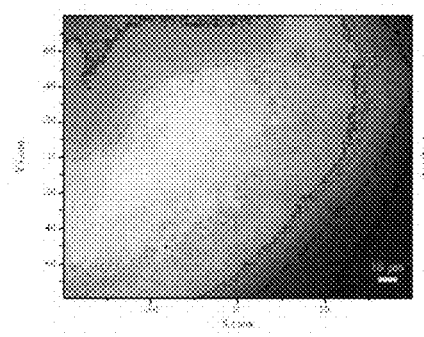
(b) Image for Eudragit RSPO
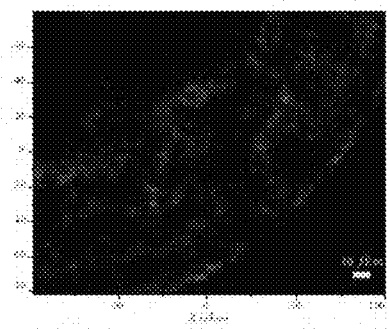
(c) Image for talc
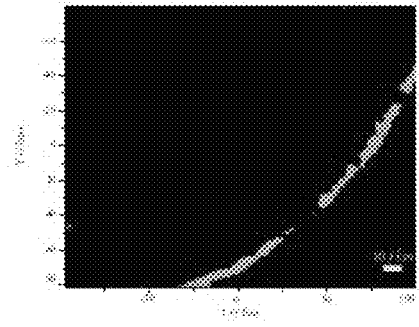
(d) Image for zonisamide
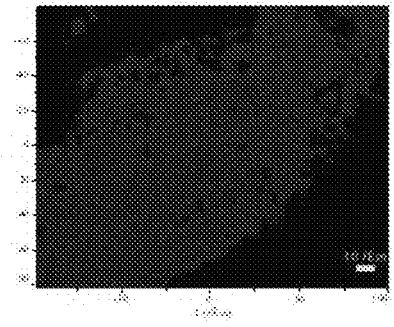
(e) Image for Eudragit RSPO, talc, and zonisamide
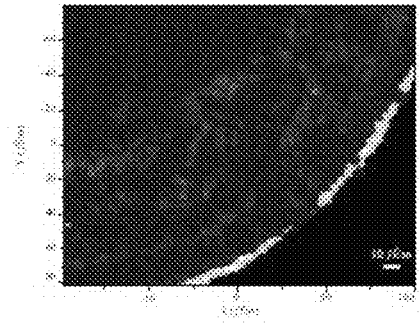

Fig.18
Results of Raman imaging on partial cross section of particles in Comparative Example 1
(a) CCD camera image
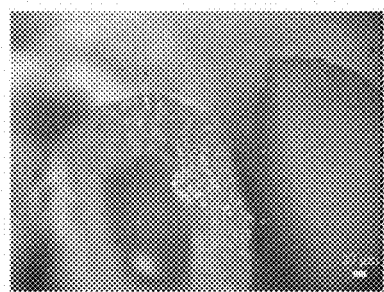
(b) Image for zonisamide
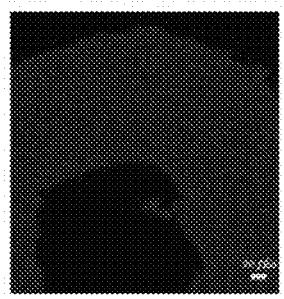
(c) Image for Eudragit RSPO
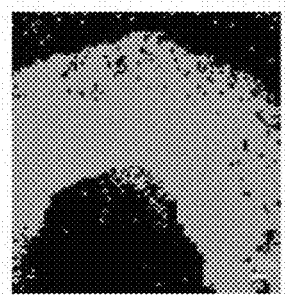
(d) Image for Eudragit RSPO and zonisamide
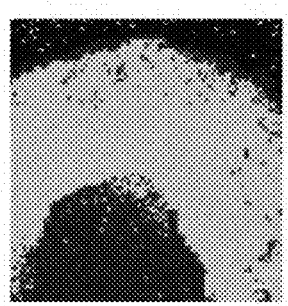

FINE PARTICLE COATING (DRUG-CONTAINING HOLLOW PARTICLE AND METHOD FOR MANUFACTURING SAME)

CROSS-REFERENCE TO RELATED APPLICATIONS

The present application is a 35 U.S.C. § 371 national stage patent application of International patent application PCT/JP2018/038895, filed on Oct. 18, 2018, which is based on and claims the benefits of priority to Japanese Application No. 2017-254309, filed on Dec. 28, 2017. The entire contents of these applications are incorporated herein by reference.

TECHNICAL FIELD

The present invention relates to a novel microparticle coating. The present invention relates to a coating method that is efficient and requires a short period of time. The present invention relates to coatable microparticles.

BACKGROUND ART

For solid pharmaceutical formulations, drug containing particles are generally manufactured by granulating only a drug or a drug mixed with another formulation component, and then further granulating by mixing another component, mixing another granule, or adding another component to prepare a tablet, a granule, or capsule agent by filling a capsule with the particles.

Furthermore, in order to have a drug absorbed at a desired site at a desired time to attain a desired efficacy, the drug containing particles themselves needed to be imparted with enteric, stomach soluble, or other desired functionality, or subjected to processing that can impart a desired function thereon. Oral release controlling technologies include a single unit type, which uses one carrier for releasing a drug, and a multiple unit type, which uses multiple carriers for releasing a drug. A multiple unit type formulation quickly diffuses and disperses into a digestive tract after oral ingestion. For this reason, multiple unit type formulations are less likely to be affected by bioactivity than single unit types and can reduce a topical increase in drug concentration in the body, such that multiple unit type formulations are more preferably used than single type units. Multiple unit types are roughly divided into a matrix type, in which a drug is dispersed in a carrier such as a macromolecule to control the release, and a coating type, in which a release controlling coating film is formed on drug containing particles to control the release. The coating type has a higher ability to control release than the matrix type, and the degree of control of release can be readily changed. Thus, the coating type is frequently used when precise control of release is required (Non Patent Literature 1). Patent Literature 1 discloses a manufacturing method for spraying a solvent with a release controlling macromolecule dissolved therein to coat drug containing nuclear particles using a fluidized bed granulator (Wurster fluidized bed granulator). Patent Literature 2 discloses a manufacturing method that applies heat in a stirring granulator and melts and fuses a release controlling macromolecule to a drug containing nuclear particles comprising fatty acids. Patent Literature 3 discloses a manufacturing method for coating drug containing particles with a rolling fluidized bed coating apparatus.

A method of dissolving a release controlling macromolecule into a solvent and spraying the solution has a problem in that the ability to control release of coated particles is high, but the coating takes a long period of time, and the production yield is low for each manufacture. It is possible to reduce the coating time or improve the production yield to solve the problem, but this instead results in a problem of reduced ability to control release of coated particles, and difficulty in adjusting the degree of controlling release. In this manner, it was difficult to simultaneously achieve release controlling ability and productivity.

CITATION LIST

Patent Literature

[PTL 1] Japanese Laid-Open Publication No. 2016-65021
[PTL 2] Japanese Patent No. 4592590
[PTL 3] International Publication No. WO 2002/060448

Non Patent Literature

[NPL 1] Shajahan Abdul, Anil V. Chandewar, Sunil B. Jaiswal., 2010. A flexible technology for modified-release drugs: Multiple-unit pellet system (MUPS). J. Control. Release. 147, 2-16.

SUMMARY OF INVENTION

Solution to Problem

The inventors, as a result of diligent study, have found that particles comprising a coating layer enhancing the release controlling function of a macromolecule can be efficiently manufactured by a very simple means of mixing nuclear particles comprising a macromolecule with an additive and stirring and granulating while spraying a solvent that can dissolve a macromolecule to complete the present invention.
(Item 1)
A manufacturing method of particles coated with coatable microparticles, comprising the step of adding the coatable microparticles to an inner core comprising a drug and a macromolecule, and, while rolling the mixture, coating the mixture while spraying a solvent that can dissolve the macromolecule, wherein the particles coated with the coatable microparticles are drug-containing hollow particles.
(Item 2)
The manufacturing method of item 1, wherein a D90 value of the coatable microparticles is less than 100 μm.
(Item 3)
The manufacturing method of any one of items 1 to 2, wherein a mean particle size of the coatable microparticles is less than 25 μm.
(Item 4)
The manufacturing method of any one of items 1 to 3, wherein a D100 value of the coatable microparticles is less than 150 μm.
(Item 5)
The manufacturing method of any one of items 1 to 4, wherein all of the coatable microparticles pass through a 100 mesh sieve.
(Item 6)
The manufacturing method of any one of items 1 to 5, wherein the coatable microparticles are selected from one or more of celluloses, stearic acid, stearate, talc, oil and fat, metal oxide, stearyl fumarate salt, and alginic acid.

(Item 7)

The manufacturing method of any one of items 1 to 6, wherein the coatable microparticles are selected from one or more of talc, Red Ferric Oxide, Yellow Ferric Oxide, titanium oxide, sodium stearyl fumarate, and sodium stearate.

(Item 8)

A composition for imparting a sustained release, enteric, stomach soluble, bitterness masking, or photostable function to drug-containing hollow particles consisting of a shell and a hollow section, comprising coatable microparticles.

(Item 9)

A composition for conferring a sustained release property to drug-containing hollow particles consisting of a shell and a hollow section, comprising coatable microparticles.

(Item 10)

The composition of items 8 or 9, wherein a D90 value of the coatable microparticles is less than 100 μm.

(Item 11)

The composition of any one of items 8 to 10, wherein a mean particle size of the coatable microparticles is less than 25 μm.

(Item 12)

The composition of any one of items 8 to 11, wherein a D100 value of the coatable microparticles is less than 150 μm.

(Item 13)

The composition of any one of items 8 to 12, wherein all of the coatable microparticles pass through a 100 mesh sieve.

(Item 14)

The composition of any one of items 8 to 13, wherein the coatable microparticles are selected from the group consisting of celluloses, stearic acid, stearate, talc, oil and fat, metal oxide, stearyl fumarate salt, and alginic acid.

(Item 15)

The composition of any one of items 8 to 14, wherein the coatable microparticles are selected from the group consisting of talc, Red Ferric Oxide, Yellow Ferric Oxide, titanium oxide, sodium stearyl fumarate, and sodium stearate.

(Item 16)

The composition of any one of items 8 to 15, wherein the shell comprises the drug and the macromolecule.

(Item 17)

Particles coated with coatable microparticles, comprising the same macromolecule in an inner core layer and a coating layer, wherein the coatable microparticles further enhance a property of the macromolecule of an inner core, and the inner core layer comprises a hollow section.

(Item 18)

The particles of item 17, wherein a D90 value of the coatable microparticles is less than 100 μm.

(Item 19)

The particles of item 17 or 18, wherein a mean particle size of the coatable microparticles is less than 25 μm.

(Item 20)

The particles of any one of items 17 to 19, wherein a D100 value of the coatable microparticles is less than 150 μm.

(Item 21)

The particles of any one of items 17 to 20, wherein all of the coatable microparticles pass through a 100 mesh sieve.

(Item 22)

The particles of any one of items 17 to 21, wherein the coatable microparticles are selected from one or more of celluloses, stearic acid, stearate, talc, oil and fat, metal oxide, stearyl fumarate salt, and alginic acid.

(Item 23)

The particles of any one of items 17 to 22, wherein the coatable microparticles are selected from one or more of talc, Red Ferric Oxide, Yellow Ferric Oxide, titanium oxide, sodium stearyl fumarate, and sodium stearate.

(Item 1A)

A manufacturing method of particles coated with coatable microparticles, comprising the step of adding the coatable microparticles to an inner core comprising a component of interest and a macromolecule, and, while rolling the resulting mixture, coating the mixture while spraying a solvent that can dissolve the macromolecule, wherein the particles coated with the coatable microparticles are coated component of interest-containing hollow particles.

(Item 2A)

The manufacturing method of item 1A, wherein a D90 value of the coatable microparticles is 100 μm or less.

(Item 3A)

The manufacturing method of item 1A or 2A, wherein a mean particle size of the coatable microparticles is 25 μm or less.

(Item 4A)

The manufacturing method of any one of items 1A to 3A, wherein a D100 value of the coatable microparticles is 150 μm or less.

(Item 5A)

The manufacturing method of any one of items 1A to 4A, wherein all of the coatable microparticles pass through a 100 mesh sieve.

(Item 6A)

The manufacturing method of any one of items 1A to 5A, wherein the coatable microparticles are selected from one or more of celluloses, stearic acid, stearate, talc, oil and fat, metal oxide, stearyl fumarate salt, and alginic acid.

(Item 7A)

The manufacturing method of any one of items 1A to 6A, wherein the coatable microparticles are selected from one or more of talc, Red Ferric Oxide, Yellow Ferric Oxide, titanium oxide, sodium stearyl fumarate, and sodium stearate.

(Item 8A)

The manufacturing method of any one of items 1A to 7A, wherein the component of interest is a drug, a quasi-drug, a cosmetic, an agricultural chemical, a supplement, or a food product.

(Item 9A)

A composition for imparting a sustained release, enteric, stomach soluble, bitterness masking, or photostable function to component of interest-containing hollow particles that are nuclear particles consisting of a shell and a hollow section, comprising coatable microparticles.

(Item 10A)

A composition for imparting a function based on at least one property to component of interest-containing hollow particles that are nuclear particles consisting of a shell and a hollow section, comprising coatable microparticles, which can impart the property.

(Item 11A)

A composition for imparting a photostable function to component of interest-containing hollow particles that are nuclear particles consisting of a shell and a hollow section, comprising coatable microparticles.

(Item 12A)

A composition for enhancing a property of a macromolecule of component of interest-containing hollow particles that are nuclear particles consisting of a shell comprising a shell and a macromolecule and a hollow section, comprising coatable microparticles.

(Item 13A)

A composition for enhancing a sustained release, enteric, stomach soluble, or bitterness masking property of component of interest-containing hollow particles that are nuclear particles consisting of a shell and a hollow section, comprising coatable microparticles.

(Item 14A)

A composition for conferring a sustained release property to component of interest-containing hollow particles that are nuclear particles consisting of a shell and a hollow section, comprising coatable microparticles.

(Item 15A)

The composition of any one of items 8A to 14A, wherein a D90 value of the coatable microparticles is 100 μm or less.

(Item 16A)

The composition of any one of items 8A to 15A, wherein a mean particle size of the coatable microparticles is 25 μm or less.

(Item 17A)

The composition of any one of items 8A to 16A, wherein a D100 value of the coatable microparticles is 150 μm or less.

(Item 18A)

The composition of any one of items 8A to 17A, wherein all of the coatable microparticles pass through a 100 mesh sieve.

(Item 19A)

The composition of any one of items 8A to 18A, wherein the coatable microparticles are selected from the group consisting of celluloses, stearic acid, stearate, talc, oil and fat, metal oxide, stearyl fumarate salt, and alginic acid.

(Item 20A)

The composition of any one of items 8A to 18A, wherein the coatable microparticles are selected from the group consisting of talc, Red Ferric Oxide, Yellow Ferric Oxide, titanium oxide, sodium stearyl fumarate, and sodium stearate.

(Item 21A)

The composition of any one of items 8A to 20A, wherein the shell comprises the component of interest and the macromolecule.

(Item 22A)

The composition of any one of items 8A to 21A, wherein the component of interest is a drug, a quasi-drug, a cosmetic, an agricultural chemical, a supplement, or a food product.

(Item 23A)

Particles coated with coatable microparticles, comprising the same macromolecule in an inner core layer and a coating layer, wherein the coatable microparticles further enhance a property of the macromolecule of an inner core, and the inner core layer comprises a hollow section.

(Item 24A)

The particles of item 23A, wherein a D90 value of the coatable microparticles is 100 μm or less.

(Item 25A)

The particles of item 23A or 24A, wherein a mean particle size of the coatable microparticles is 25 μm or less.

(Item 26A)

The particles of any one of items 23A to 25A, wherein a D100 value of the coatable microparticles is 150 μm or less.

(Item 27A)

The particles of any one of items 23A to 26A, wherein all of the coatable microparticles pass through a 100 mesh sieve.

(Item 28A)

The particles of any one of items 23A to 27A, wherein the coatable microparticles are selected from one or more of celluloses, stearic acid, stearate, talc, oil and fat, metal oxide, stearyl fumarate salt, and alginic acid.

(Item 29A)

The particles of any one of items 23A to 28A, wherein the coatable microparticles are selected from one or more of talc, Red Ferric Oxide, Yellow Ferric Oxide, titanium oxide, sodium stearyl fumarate, and sodium stearate.

The present invention is intended so that one or more of the above features can be provided as the explicitly disclosed combinations as well as other combinations thereof. Additional embodiments and advantages of the present invention are recognized by those skilled in the art by reading and understanding the following detailed explanation, as needed.

Advantageous Effects of Invention

The present invention provides a coating method that is efficient and requires a short period of time. The present invention also provides a method that improves the coatability (coating time and coverage).

The coated component of interest-containing hollow particles of the invention can enhance the ability to control release of a polymer contained in nuclear particles. Specifically, a desired functionality (e.g., enteric, stomach soluble, sustained release, bitterness masking, or photostable function or the like) can be imparted by selecting a polymer contained in nuclear particles, so that it is possible to provide a formulation, which attains a desired efficacy by having a component of interest absorbed at a desired site at a desired time. Furthermore, the particles size and particle size distribution of coated component of interest-containing hollow particles can be controlled in any manner by selecting the particle size and particle size distribution of nuclear particles, so that particles matching the objective can be readily manufactured.

BRIEF DESCRIPTION OF DRAWINGS

FIG. 1 shows the appearance of nuclear particles in Comparative Example 1.

FIG. 2 shows the appearance of coated particles in Example 1-1.

FIG. 3 shows results of dissolution tests in Comparative Example 2, Example 2-1, Example 2-2, and Example 2-3.

FIG. 4 shows results of dissolution tests conducted using particles manufactured in Example 4 and particles manufactured in Comparative Example 1.

FIG. 5 shows results of dissolution tests conducted using particles manufactured in Example 5 and particles manufactured in Comparative Example 1.

FIG. 6 shows results of dissolution tests conducted using tablets manufactured in Example 8-1 and tablets manufactured in Comparative Example 8-1.

FIG. 7 shows results of dissolution tests conducted using tablets manufactured in Example 8-1 and tablets manufactured in Comparative Example 8-1.

FIG. 8 shows results of dissolution tests conducted using particles manufactured in Example 7-2 and tablets manufactured in Comparative Example 8-2.

FIG. 9 shows results of dissolution tests conducted using particles manufactured in Example 7-2 and tablets manufactured in Comparative Example 8-2.

FIG. 10 shows results of photostability test on particles manufactured in Example 9 and Comparative Example 9.

FIG. 11 shows particles containing multiple active pharmaceutical ingredients of Example 10.

FIG. 12 shows results of sensory evaluation tests conducted using tablets manufactured in Example 13-2 and Comparative Example 13-2.

FIG. 17 shows results of Raman imaging on a partial cross-section of the particles in Example 1-3.

FIG. 18 shows results of Raman imaging on a partial cross-section of the particles in Comparative Example 1.

DESCRIPTION OF EMBODIMENTS

Figure 13:
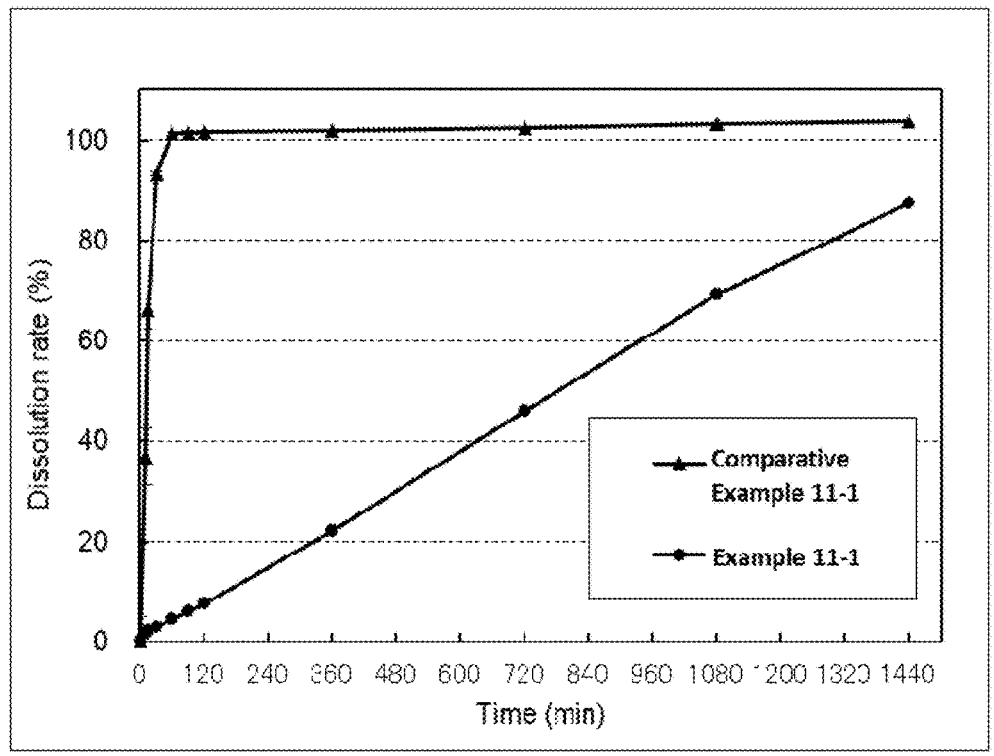
FIG. 13 shows results of dissolution tests of Example 11-1 and Comparative Example 11-1.

The present invention is described in detail hereinafter. Throughout the entire specification, a singular expression should be understood as encompassing the concept thereof in plural form, unless specifically noted otherwise. Thus, singular articles (e.g., "a", "an", "the", and the like in the case of English) should also be understood as encompassing the concept thereof in plural form, unless specifically noted otherwise. Further, the terms used herein should be understood to be used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

The present invention is further described in detail hereinafter.

The component of interest-containing hollow particles of the invention has a component of interest and a macromolecule as essential constituents. The particle also refers to one particle as well as a collection of a plurality of particles.

As used herein, "mean particle size" refers to cumulative 50% point of particle size D50 in volume based measurement of powder particles. Such a mean particle size is measured based on volume with a laser diffraction particle size distribution analyzer (e.g., Powrex Corp: PARTICLE VIEWER, Shimadzu Corp: SALD-3000J, or SYMPATEC: HELOS & RODOS).

(I) Component of Interest

The component of interest can be used without any particular limitation. Examples of "component of interest" used in the method of the invention include components, such as active ingredients of drugs or the like used in drugs, quasi-drugs, or cosmetics, agricultural chemicals, supplements, and food products. A component of interest can also be used by mixing one or more components of interest. In specific embodiments in the food product industry, a product comprising the component of interest of the invention can be used in a functional product, food for specified health uses, food with nutrient function claims, food with function claims, general food product, or the like.

A drug can be used without any particular limitation. Any drug or compound can be used as the "drug" used in the method of the invention, regardless of the property such as basic, acidic, amphoteric, or neutral, solubility, or heat resistance. Among them, it is preferable that a drug is crystalline from the viewpoint of stability and ease of handling. A drug can also be used by mixing one or more drugs.

The component of interest used in the present invention can be any component of interest. Examples thereof include revitalizing health drug; antipyretic analgesic anti-inflammatory drug; antipsychotic drug; sedative hypnotic drug; antispasmodics; central nervous system agonist; cerebral metabolism improving drug; cerebral circulation improving drug; antiepileptic drug; sympathomimetic; digestant; antiulcer agent; gastrointestinal motility improving agent; antacid; antitussive expectorant; intestinal motility depressant; antiemetic agent; respiratory stimulant; bronchodilator; allergy drug; antihistamine; cardiotonic agent; arrhythmia agent; diuretic; ACE inhibitor; Ca antagonist; AII antagonist; vasoconstrictor; coronary vasodilator; vasodilator; peripheral vasodilator; hyperlipidemia agent; cholagogue; cephem antibiotic; oral antimicrobial agent; chemotherapeutic agent; sulfonylurea drug; α glucosidase inhibitor; insulin sensitizer; fast-acting insulin secretagogue; DPPIV inhibitor; therapeutic agent for diabetic complications; osteoporosis agent; anti-rheumatic agent; skeletal muscle relaxant; alkaloid narcotic; sulfa agent; gout treating agent; blood coagulation inhibitor; antineoplastic agent; and the like.

Specific examples of the components of interest of the invention include revitalizing health drugs such as vitamins, minerals, amino acids, crude drugs, and lactic acid bacteria; antipyretic analgesic anti-inflammatory drugs such as aspirin, acetaminophen, ethenzamide, ibuprofen, caffeine, and indomethacin; antipsychotic drugs such as blonanserin, lurasidone hydrochloride, tandospirone citrate, perospirone hydrochloride, reserpine, diazepam, fludiazepam, haloperidol, aripiprazole, and nortriptyline hydrochloride; sedative hypnotic drugs such as nitrazepam, diazepam, triazolam, brotizolam, zolpidem, and nimetazepam; antispasmodics such as scopolamine hydrobromide; central nervous system agonists such as zonisamide, droxidopa, citicoline, biperiden hydrochloride, and donepezil hydrochloride; cerebral metabolism improving drugs such as meclofenoxate hydrochloride; cerebral circulation improving drugs such as vinpocetine; antiepileptic drugs such as zonisamide, phenytoin, clonazepam, primidone, sodium valproate, carbamazepine, diazepam, ethotoin, and acetylphenetride; sympathomimetics such as isoproterenol hydrochloride; digestants such as diastase, scopolia extract, and pancreatin; antiulcer agents such as cimetidine, lansoprazole, famotidine, sulpiride, and gefarnate; gastrointestinal motility improving agents such as mosapride citrate; antacids such as magnesium aluminometasilicate; antitussive expectorants such as cloperastine hydrochloride, ephedrine hydrochloride, and pentoxyverine citrate; intestinal motility depressants such as loperamide hydrochloride; antiemetic agents such as difenidol hydrochloride; respiratory stimulants such as levallorphan tartrate; bronchodilators such as theophylline; allergy drugs such as ebastine; antihistamines such as diphenhydramine hydrochloride; cardiotonic agents such as caffeine and digoxin; arrhythmia agents such as procainamide hydrochloride and arotinolol hydrochloride; diuretics such as isosorbide; ACE inhibitors such as delapril hydrochloride, captopril, and alacepril; Ca antagonists such as nifedipine, diltiazem hydrochloride, manidipine hydrochloride, and amlodipine besylate; AII antagonists such as candesartan, olmesartan, and valsartan; vasoconstrictors such as phenylephrine hydrochloride; coronary vasodilators such as carbocromen hydrochloride; vasodilators such as limaprost alfadex; peripheral vasodilators such as cinnarizine; hyperlipidemia agents such as simvastatin and pravastatin sodium; cholagogues such as dehydrocholic acid; cephem antibiotics such as cephalexin and cefaclor; oral antimicrobial agents such as gatifloxacin and sparfloxacin; chemotherapeutic agents such as sulfamethizole and pipemidic acid trihydrate; sulfonylurea drugs such as gliclazide, glibenclamide, and glimepiride; a glucosidase inhibitors such as acarbose, voglibose, and miglitol; insulin sensitizers such as pioglitazone hydrochloride and rosiglitazone; biguanide drugs such as metformin, buformin, and phenformin; fast-acting insulin secretagogues such as nateglinide and mitiglinide calcium hydrate; DPPIV inhibitors such as sitagliptin; therapeutic agents for diabetic complications such as ranirestat and epalrestat; osteoporosis agents such as etidronate disodium; anti-rheumatic agents such as methotrexate; skeletal muscle relaxants such as methocarbamol; antidizziness agents such as meclizine hydrochloride; alkaloid narcotics such as morphine hydrochloride and opium; sulfa agents such as sulfisomidine; gout treating agents such as allopurinol; blood coagulation inhibitors such as dicoumarol; antineoplastic agents such as 5-fluorouracil, mitomycin; and the like.

The component of interest in the present invention can be selected from indomethacin, blonanserin, lurasidone hydrochloride, tandospirone citrate, perospirone hydrochloride, fludiazepam, haloperidol, nortriptyline hydrochloride, nimetazepam, zonisamide, droxidopa, biperiden hydrochloride, phenytoin, clonazepam, primidone, sodium valproate, ethotoin, acetylphenetride, pancreatin, cimetidine, sulpiride, gefarnate, mosapride citrate, ephedrine hydrochloride, pentoxyverine citrate, arotinolol hydrochloride, alacepril, amlodipine besylate, gatifloxacin, sparfloxacin, pipemidic acid trihydrate, gliclazide, miglitol, ranirestat, disodium etidronate, allopurinol, and the like.

When the present invention is used as a drug, the components of interest listed above can be in a salt or free form other than those described above, as long as they are pharmaceutically acceptable. The components of interest can also be in a form of a solvate such as an alcohol solvate or a hydrate. The blending ratio of a component of interest herein includes moisture of hydrate, solvent of solvate, and/or salt contained in the component of interest. The component of interest listed above can be used alone or by combining two or more components. A component of interest which has been treated to mask an unpleasant taste such as bitterness can also be used. Examples of masking include coating of an active ingredient.

The mean particle size of components of interest is not particularly limited, and can change in the process of manufacturing coated component of interest-containing hollow particles or the like.

The present invention can manufacture not only coated component of interest-containing hollow particles comprising a component of interest at a low content rate, but also those comprising a component of interest at a high content rate (e.g., 50 to 96% by weight, preferably 70 to 96% by weight, and more preferably 90 to 96% by weight per 100% by weight of the coated component of interest-containing hollow particles).

In the present invention, a component of interest can be in any part of the coated component of interest-containing hollow particles. Specifically, a component of interest can be in a nuclear particle, in a coating layer, between coating layers, or in the outermost layer.

(II) Macromolecule

As used herein, "macromolecule" refers to a molecule with a large relative molecular mass, having a structure composed of numerous repeats of molecules with a small relative molecular mass, and refers especially to a functional macromolecule. The "molecule with a large relative molecular mass" refers to those with a mean molecular weight (weight average molecular weight: measured by light scattering method) of generally 1000 or greater, preferably 5000 or greater, and more preferably 10000 or greater. While the upper limit of molecular weight is not particularly limited, it is preferably 10000000 or less, more preferably 5000000 or less, still more preferably 2000000 or less, and especially preferably 1000000 or less. Examples of functional macromolecules include water insoluble macromolecules, enteric macromolecules, and stomach soluble macromolecules. Preferred examples thereof include water insoluble macromolecules, enteric macromolecules, and stomach soluble macromolecules. One or more macromolecules can be mixed and used.

Examples of water insoluble macromolecules include water-insoluble cellulose ethers such as ethyl cellulose (e.g., trade name: ETHOCEL (ETOCEL 10P)) and cellulose acetate, water-insoluble acrylic acid copolymers such as aminoalkyl methacrylate copolymer RS (e.g., trade name: Eudragit RL 100, Eudragit RLPO, Eudragit RL 30 D, Eudragit RS 100, Eudragit RSPO, and Eudragit RS 30 D) and ethyl acrylate-methyl methacrylate copolymer dispersion (e.g., Eudragit NE 30 D), vinyl acetate resin, and the like. One or more can be mixed and used. Preferred examples thereof include ethyl cellulose and aminoalkyl methacrylate copolymer RS. The present invention can impart a function of sustained release or a bitterness masking for a component of interest having bitterness by using a water insoluble macromolecule as the macromolecule.

Examples of enteric macromolecules include hydroxypropyl methyl cellulose acetate succinate (e.g., trade name: AQOAT LF, AQOAT MF, AQOAT HF, AQOAT LG, AQOAT MG, AQOAT HG), hydroxypropyl methyl cellulose phthalate (e.g., trade name: HPMCP 50, HPMCP 55, HPMCP 55S), methacrylic acid copolymers such as methacrylic acid copolymer L (e.g., trade name: Eudragit L 100), methacrylic acid copolymer LD (e.g., trade name: Eudragit L 30D-55), dried methacrylic acid copolymer LD (e.g., trade name: Eudragit L 100-55), methacrylic acid copolymer S (e.g., trade name: Eudragit S 100), and methacrylic acid-N-butyl acrylate copolymer, and the like, one or more of which can be mixed and used. Preferred examples thereof include methacrylic acid copolymer L and dried methacrylic acid copolymer LD.

Examples of stomach soluble macromolecules include stomach soluble polyvinyl derivatives such as polyvinyl acetal diethyl aminoacetate, stomach soluble acrylic acid based copolymers such as aminoalkyl methacrylate copolymer E (e.g., trade name: Eudragit E 100 and Eudragit EPO), one or more of which can be mixed and used. Preferred examples thereof include aminoalkyl methacrylate copolymer E.

In the present invention, a macromolecule can be selected in accordance with the objective. To attain sustained release of a component of interest, it is preferable to use a water insoluble macromolecule as the macromolecule. To achieve bitterness masking, it is preferable to use a water insoluble macromolecule, enteric macromolecule, stomach soluble macromolecule, or the like. To suppress the dissolution of a component of interest in the stomach and to quicken the dissolution in the small intestine, it is preferable to use an enteric macromolecule. An additional macromolecule other than those described above can be used to form a complex and used depending on the objective. For example, two or more macromolecules with different functions such as a water soluble macromolecule and a water insoluble macromolecule can be mixed and used.

The macromolecules in the present invention are in nuclear particles before the manufacture, and are dispersed in coated component of interest-containing hollow particles after the manufacture of the coated component of interest-containing hollow particles. The present invention does not use a macromolecule as a granulation solution in a form of a solution or suspension, but in a form that is present in nuclear particles. The present invention is characterized by granulation while adding, e.g., spraying, a solvent thereafter. However, some of the macromolecules or components of interest can be dissolved or suspended in a solvent for use, to the extent that the effect of the present invention is attained. The amount of macromolecule used varies depending on the component of interest, amount of another additive, particle size, strength of binding force of the macromolecule, or the like, but a macromolecule is generally used in the range of 4 to 50% by weight, preferably 4 to 40% by weight, more preferably 6 to 40% by weight or 8 to 40% by weight, still more preferably 10 to 40% by weight, still yet more preferably 10 to 30% by weight, and especially preferably 10 to 20% by weight per 100% by weight of coated component of interest-containing hollow particles to be manufactured.

(III) Nuclear Particles

As used herein, nuclear particles refer to all particles that comprise a macromolecule in the coating step of this technology and dissolves with a solvent to be sprayed. For example, when coated component of interest-containing hollow particles obtained in the coating step of the invention are used again in the coating step of the invention, the coated component of interest-containing hollow particles are also considered nuclear particles in the new step. Coated particles refer to particles coated with coatable microparticles.

Nuclear particles may or may not comprise a component of interest. Examples of component of interest include, but are not particularly limited to, drugs, quasi-drugs, cosmetics, agricultural chemicals, supplements, and food products.

(IV) Additive

The additives of the invention are not particularly limited, as long as they are additives that are commonly used. Examples thereof include excipients (e.g., starch such as rice starch, D-mannitol, and magnesium carbonate), binding agents, sweeteners, corrigents (taste or odor), flavoring agents, fluidizers (e.g., AEROSIL), antistatic agents, colorants, disintegrants, lubricants, plasticizers, deflocculating agents, coating agents, and the like. While the additive is not particularly limited, the additive can be blended without exerting a function of the macromolecule of the invention when the additive does not dissolve in the solvent used, even those falling under the macromolecules described above.

(V) Coatable Microparticles

As used herein, "microparticles" have a size equal to or less than "particles". "Particles" and "microparticles" are used in the normal meaning of the art. In relation to the present invention, "particles" indicate especially those comprising a component of interest, and "microparticles" indicate those for coating. For this reason, the terms are used as in "particles coated with coatable microparticles" herein. In such a case, the "particles" comprise a component of interest, a macromolecule, and the like in addition to "coatable microparticles".

The coatable microparticles in the invention can be any particle that can accumulate on the outer portion of nuclear particles. In other words, coatable microparticles can be a component of interest, a macromolecule, or an additive, as long as it can accumulate on nuclear particles. Coatable microparticles can also be a mixture thereof.

In the coating step of coated component of interest-containing hollow particles, the mean particle size of nuclear particles is preferably 5-fold or greater, preferably 10-fold or greater, more preferably 15-fold or greater, still more preferably 20-fold or greater, and especially preferably 25-fold or greater than the mean particle size of coatable microparticles consisting of a component of interest, macromolecule, and/or additive, and is generally 10000000-fold or less. The component of interest-containing hollow particles that are nuclear particles can be manufactured in accordance with the method described in WO 2014/030656 "MEDICAMENT-CONTAINING HOLLOW PARTICLE" to give a predetermined particle size.

The D50 value of the coatable microparticles of the invention is preferably less than 100 µm, less than 90 µm, less than 80 µm, less than 70 µm, less than 60 µm, less than 50 µm, less than 40 µm, less than 30 µm, less than 20 µm, or less than 10 µm. The D50 value of the coatable microparticles of the invention is preferably 100 µm or less, 90 µm or less, 80 µm or less, 70 µm or less, 60 µm or less, 50 µm or less, 40 µm or less, 30 µm or less, 20 µm or less, or 10 µm or less. The D50 value of the coatable microparticles of the invention is preferably 0.5 µm or greater, 0.8 µm or greater, 1 µm or greater, or 1.5 µm or greater. The D50 value of the coatable microparticles of the invention is preferably greater than 0.5 µm, greater than 0.8 µm, greater than 1 µm, or greater than 1.5 µm.

The D90 value of the coatable microparticles of the invention is preferably less than 200 µm, less than 190 µm, less than 180 µm, less than 170 µm, less than 160 µm, less than 150 µm, less than 140 µm, less than 130 µm, less than 120 µm, less than 110 µm, less than 100 µm, less than 90 µm, less than 80 µm, less than 70 µm, less than 60 µm, less than 50 µm, less than 40 µm, less than 30 µm, less than 20 µm, or less than 10 µm. The D90 value of the coatable microparticles of the invention is preferably 200 µm or less, 190 µm or less, 180 µm or less, 170 µm or less, 160 µm or less, 150 µm or less, 140 µm or less, 130 µm or less, 120 µm or less, 110 µm or less, 100 µm or less, 90 µm or less, 80 µm or less, 70 µm or less, 60 µm or less, 50 µm or less, 40 µm or less, 30 µm or less, 20 µm or less, or 10 µm or less. The D90 value of the coatable microparticles of the invention is preferably 1 µm or greater, 2 µm or greater, 3 µm or greater, or 4 µm or greater. The D90 value of the coatable microparticles of the invention is preferably greater than 1 µm, greater than 2 µm, greater than 3 µm, or greater than 4 µm.

The D99 value of the coatable microparticles of the invention is preferably less than 200 µm, less than 190 µm, less than 180 µm, less than 170 µm, less than 160 µm, less than 150 µm, less than 140 µm, less than 130 µm, less than 120 µm, less than 110 µm, less than 100 µm, less than 90 µm, less than 80 µm, less than 70 µm, less than 60 µm, less than 50 µm, less than 40 µm, less than 30 µm, less than 20 µm, or less than 10 µm. The D99 value of the coatable microparticles of the invention is preferably 200 µm or less, 190 µm or less, 180 µm or less, 170 µm or less, 160 µm or less, 150 µm or less, 140 µm or less, 130 µm or less, 120 µm or less, 110 µm or less, 100 µm or less, 90 µm or less, 80 µm or less, 70 µm or less, 60 µm or less, 50 µm or less, 40 µm or less, 30 µm or less, 20 µm or less, or 10 µm or less. The D99 value of the coatable microparticles of the invention is preferably 1 µm or greater, 3 µm or greater, 5 µm or greater, or 7 µm or greater. The D99 value of the coatable microparticles of the invention is preferably greater than 1 µm, greater than 3 µm, greater than 5 µm, or greater than 7 µm.

The D100 value of the coatable microparticles of the invention is preferably less than 200 µm, less than 190 µm, less than 180 µm, less than 170 µm, less than 160 µm, less than 150 µm, less than 140 µm, less than 130 µm, less than 120 µm, less than 110 µm, less than 100 µm, less than 90 µm, less than 80 µm, less than 70 µm, less than 60 µm, less than 50 µm, less than 40 µm, less than 30 µm, less than 20 µm, or less than 10 µm. The D100 value of the coatable microparticles of the invention is preferably 200 µm or less, 190 µm or less, 180 µm or less, 170 µm or less, 160 µm or less, 150 µm or less, 140 µm or less, 130 µm or less, 120 µm or less, 110 µm or less, 100 µm or less, 90 µm or less, 80 µm or less, 70 µm or less, 60 µm or less, 50 µm or less, 40 µm or less, 30 µm or less, 20 µm or less, or 10 µm or less. The D100 value of the coatable microparticles of the invention is preferably 2 µm or greater, 5 µm or greater, 7 µm or greater, or 10 µm or greater. The D100 value of the coatable microparticles of the invention is preferably greater than 2 µm, greater than 5 µm, greater than 7 µm, or greater than 10 µm.

The mean particle size of the coatable microparticles of the invention is less than 50 µm, less than 45 µm, less than 40 µm, less than 35 µm, less than 30 µm, less than 25 µm, less than 20 µm, less than 15 µm, or less than 10 µm. The means particle size of the coatable microparticles of the invention is 50 µm or less, 45 µm or less, 40 µm or less, 35 µm or less, 30 µm or less, 25 µm or less, 20 µm or less, 15 µm or less, or 10 µm or less.

All of the coatable microparticles of the invention can pass through a 100 mesh, 170 mesh, 200 mesh, 500 mesh, or 635 mesh sieve.

Examples of coatable microparticles include celluloses, lactose, lactose hydrate, saccharose, purified saccharose, purified licorice extract powder, glucose, D-mannitol, rice starch, corn starch, stearic acid, stearate, talc, oil and fat, metal oxide, fumaric acid, stearyl fumarate salt, alginic acid, alginate, ascorbic acid, aspartame, L-aspartic acid, xylitol, citric acid, citric acid hydrate, calcium citrate, sodium citrate, sodium citrate hydrate, glycine, D-xylose, L-glutamic acid, succinic acid, tartaric acid, sodium tartrate, sucralose, D-sorbitol, tannic acid, trehalose, peppermint powder, maltose hydrate, D-borneol, anhydrous citric acid, l-menthol, DL-menthol, menthol powder, green tea powder, caramel, DL-malic acid, medicinal carbon, methyl cellulose, aminoalkyl methacrylate copolymer E, aminoalkyl methacrylate copolymer RS, aminopectin, ethyl cellulose, sodium caseinate, agar, sodium agar, dioctyl sodium sulfosuccinate, sucrose fatty acid ester, purified gelatin, carboxyvinyl polymer, carboxymethyl ethyl cellulose, sodium carboxymethyl starch, hypromellose, methacrylic acid copolymer L, methacrylic acid copolymer S, copolyvidone, macromolecular polyvinylpyrrolidone, pigment, flavoring agent, benzoic acid, sodium benzoate, copper sulfate, calcium phosphate, calcium chloride, sodium phosphate, sodium chloride, calcium citrate, calcium carbonate, magnesium carbonate, calcium sulfate, magnesium chloride, sodium hydrogencarbonate, hydrous silicon dioxide, magnesium silicate, light anhydrous silicic acid, synthetic aluminum silicate, heavy anhydrous silicic acid, anhydrous silicic acid hydrate, anhydrous calcium phosphate, silicon dioxide, potassium sodium tartrate, sodium polyphosphate, metasilicic acid, aluminum sulfate, precipitated calcium carbonate, and zinc chloride. Specific examples of celluloses include crystalline cellulose, microcrystalline cellulose, crystalline cellulose carmellose sodium, carmellose, carmellose sodium, carmellose calcium, low substituted hydroxypropyl cellulose, and the like. Specific examples of stearate include sodium stearate, potassium stearate, zinc stearate, calcium stearate, aluminum stearate, magnesium stearate, polyoxyl stearate, and the like. Specific examples of oil and fat include hydrogenated castor oil, white petrolatum, polyoxyethylene powder, hydrogenated oil, cacao oil, hard wax, sodium lauryl sulfate, carnauba wax, oleic acid, rice starch, carrageenan, sucrose fatty acid ester, polyoxyethylene hydrogenated castor oil, beeswax, light fluidized paraffin, cetanol, and the like. Specific examples of metal oxides include iron oxides such as Yellow Ferric Oxide, Red Ferric Oxide, black iron oxide, brown iron oxide, and yellow iron oxide, titanium oxides, and the like. Specific examples of stearyl fumarate salt include sodium stearyl fumarate. Specific examples of alginate include sodium alginate.

Examples of coatable microparticles include celluloses, stearic acid, stearate, talc, oil and fat, metal oxide, stearyl fumarate salt, and alginic acid. Examples of coatable microparticles include talc, Red Ferric Oxide, Yellow Ferric Oxide, titanium oxide, sodium stearyl fumarate, sodium stearate, hydrogenated oil, magnesium stearate, and crystalline cellulose. Preferred examples of coatable microparticles include talc, Red Ferric Oxide, Yellow Ferric Oxide, titanium oxide, sodium stearyl fumarate, and sodium stearate.

The coatable microparticles of the invention can impart at least one property to component of interest-containing hollow particles that are nuclear particles consisting of a shell and a hollow section.

The coatable microparticles of the invention can impart a photostable function to component of interest-containing hollow particles that are nuclear particles consisting of a shell and a hollow section.

The coatable microparticles of the invention enhance a property of a macromolecule contained in an inner core. Particles coated with coatable microparticles of the invention can have, for example, improved enteric, stomach soluble, sustained release, or bitterness masking function or the like. If the coatable microparticles of the invention are used, high performance coated component of interest-containing hollow particles can be made efficiently in a short period of time.

(VI) Coated Component of Interest-Containing Hollow Particles of the Invention

The coated component of interest-containing hollow particles of the invention are those containing 0.1 to 95.9% by weight of component of interest, 4 to 40% by weight of macromolecule, and 0.1 to 95.9% by weight of coatable microparticles; preferably those comprising 1 to 94% by weight of component of interest, 5 to 30% by weight of macromolecule, and 1 to 94% by weight of additive; or those comprising 10 to 80% by weight of component of interest, 10 to 20% by weight of macromolecule, and 10 to 80% by weight of coatable microparticles and coating additives, per 100% by weight of the coated component of interest-containing hollow particles.

Examples of the coated component of interest-containing hollow particles of the invention include those comprising 60 to 96% by weight of component of interest and 4 to 40% by weight of macromolecule (preferably those comprising 70 to 95% by weight of component of interest and 5 to 30% by weight of macromolecule, more preferably those comprising 80 to 90% by weight of component of interest and 10 to 20% by weight of macromolecule) per 100% by weight of the coated component of interest-containing hollow particles, and a preferred mean particle size of nuclear particles of 5-fold or greater (preferably 15-fold or greater and more preferably 25-fold or greater) than the mean particle size of coatable microparticles.

Examples of the coated component of interest-containing hollow particles of the invention include those comprising 55 to 95.9% by weight of component of interest, 4 to 40% by weight of macromolecule, and 0.1 to 5% by weight of another additive discussed below (preferably those comprising 65 to 94.9% by weight of component of interest, 5 to 30% by weight of macromolecule, and 0.1 to 5% by weight of another additive discussed below, more preferably those comprising 75 to 89.9% by weight of component of interest and 10 to 20% by weight of macromolecule) per 100% by weight of the coated component of interest-containing hollow particles, and a preferred mean particle size of nuclear particles of 5-fold or greater (preferably 15-fold or greater and more preferably 25-fold or greater) than the mean particle size of coatable microparticles.

Examples of the coated component of interest-containing hollow particles of the invention include those comprising 0.1 to 95.9% by weight of component of interest, 4 to 40% by weight of macromolecule, and 0.1 to 95.9% by weight of another additive discussed below (preferably those comprising 1 to 94% by weight of component of interest, 5 to 30% by weight of macromolecule, and 1 to 94% by weight of another additive discussed below, more preferably those comprising 10 to 80% by weight of component of interest, 10 to 20% by weight of macromolecule, and 10 to 80% by weight of another additive discussed below) per 100% by weight of the coated component of interest-containing hollow particles, and a preferred mean particle size of nuclear particles of 5-fold or greater (preferably 15-fold or greater and more preferably 25-fold or greater) than the mean particle size of coatable microparticles.

The coated component of interest-containing hollow particles of the invention can be high performance coated component of interest-containing hollow particles. For example, enteric, stomach soluble, sustained release, bitterness masking function or the like is improved.

(VII) Component of Interest-Containing Hollow Particles that are Nuclear Particles Component of interest-containing hollow particles that are nuclear particles refer to "particles consisting of a shell (or a wall) and a hollow section, comprising a component of interest and a macromolecule in the shell" or "particles having a structure with a hollow section surrounded by a wall consisting of a composition comprising a component of interest and a macromolecule".

The feature of component of interest-containing hollow particles that are nuclear particles is in having a hollow structure inside the particles. "Hollow" in such a case refers to a single completely independent vacancy at the center of a particle surrounded by a wall (shell) of a component of interest-containing composition, unlike a state of having numerous spaces without a defined position as in normal tablets. The presence thereof can be confirmed by an electron microscope or an optical microscope.

The volume ratio of hollow section to the volume of the entire particle of component of interest-containing hollow particles that are nuclear particles is preferably about 1% to 50%, more preferably 1% to 30%, still more preferably 1.5% to 30%, and most preferably 2% to 30%. Another preferred embodiment of the volume ratio of the hollow section is about 4% to 50%, more preferably 4% to 40%, still more preferably 10% to 40%, and most preferably 10 to 30%. The volume ratio of a hollow section is found by dividing the volume of the hollow section by the volume of the particle. Since particles generally have high spheroidicity, the volume is found by assuming that the hollow section and the particle are both spheres. The volume of the hollow section and the particle can be calculated by finding the major and minor axes of the particle and hollow section at the center of the particle by an X-ray CT (computerized tomographic device) and assuming the means thereof as the hollow section diameter and particle diameter to find the volume of the spheres.

More specifically, the "volume ratio of a hollow section" in the present invention is found by calculating the following equation.

Volume ratio of a hollow section [%]=(4/3×π×(diameter of hollow section/2)$^3$)/(4/3×π×(particle size of component of interest-containing hollow particles that are nuclear particles/2)$^3$)×100

The particle size of component of interest-containing hollow particles and the diameter of a hollow section are non-destructively measured with a desktop micro-CT scanner (SKYSCAN, SKYSCAN 1172). The mean value of 10 measurements is used.

Component of interest-containing hollow particles that are nuclear particles have a wall (shell) on the outside of a hollow section. The shell can have any thickness, but a thinner shell thickness leads to weaker strength of the particle. The shell thickness is preferably 10 μm or greater, more preferably 15 μm or greater, still more preferably 20 μm or greater, and most preferably 30 μm or greater. The shell thickness can be measured with, for example, an X-ray CT (computerized tomographic device).

The shell can have any thickness ratio, which is found by the following equation. The percentage of shell thickness is preferably 20 to 80%, and more preferably 30 to 70%.

Percentage of Shell thickness [%]=(shell thickness/(particle size of component of interest-containing hollow particles that are nuclear particles/2))×100

The feature of component of interest-containing hollow particles that are nuclear particles is in the ability to freely adjust the particle size. Therefore, particles can be adjusted to have a mean particle size of about 1 to 7000 μm, preferably about 5 to 1000 μm, more preferably about 10 to 500 μm, still more preferably about 10 to 400 μm, still more preferably about 20 to 300 μm, and most preferably about 50 to 300 μm.

From the viewpoint of particle strength, the particle size is preferably about 50 to 7000 μm, more preferably about 50 to 1000 μm, and still more preferably about 50 to 500 μm. From another viewpoint, particles can be adjusted to have a particle size of preferably about 70 to 7000 μm, more preferably about 70 to 1000 μm, still more preferably about 70 to 500 μm, especially preferably about 70 to 300 μm, and most preferably about 100 to 300 μm.

In the present invention, the size of component of interest-containing hollow particles that are nuclear particles can be adjusted by adjusting the mean particle size of the macromolecule.

The diameter of a hollow section is generally 10 μm or greater in component of interest-containing hollow particles that are nuclear particles. The diameter of the hollow section can be adjusted freely, generally to about 10 to 5000 μm, preferably to about 20 to 700 μm, more preferably to about 30 to 300 μm, and still more preferably to about 50 to 200 μm. The ratio of the hollow section can be freely adjusted to match the particle size.

In one embodiment, component of interest-containing hollow particles that are nuclear particles has a "smooth surface". As used herein, smooth surface means absence of protrusion, and the surface does not have convex or concave. Since fluidity of component of interest-containing hollow particles that are nuclear particles to be filled is required when filling the particles upon making tablets, capsules or the like, the component of interest-containing hollow particles that are nuclear particles preferably have a smooth surface. Component of interest-containing hollow particles that are nuclear particles preferably have a smooth surface because efficiency is enhanced when applying a coating to impart additional functionality to the component of interest-containing hollow particles that are nuclear particles. For example, such smoothness of surface can be observed visually. For visual observation, the particles can be magnified with a microscope or the like for observation. The evaluation thereof is represented by "very smooth" (+++), "smooth" (++), "rather smooth" (+), and "not smooth" (−). "Very smooth" shows absence of a clear protrusion on the particle surface, and the surface does not have convex or concave. "Smooth" shows absence of a clear protrusion on the particle surface, but the surface has gentle concave or convex. "Rather smooth" shows presence of a clear protrusion or clear convex or concave on the particle surface. "Not smooth" shows presence of a clear protrusion and a clear convex or concave on the particle surface. Component of interest-containing hollow particles that are nuclear particles may be "not smooth", preferably "very smooth", "smooth" or "rather smooth", more preferably "very smooth" or "smooth", further preferably "very smooth". 3D laser Scanning confocal microscope VK-X200 (KEYENCE) may be used for the measurement. The "smooth surface" specifically means that the surface roughness (Ra value) measured by the above-mentioned tool is not more than 3.5, preferably not more than 2.5, more preferably not more than 1.5.

The surface smoothness is affected by the ratio of mean particle sizes of a macromolecule and component of interest and/or another additive.

In one embodiment, component of interest-containing hollow particles that are nuclear particles is spherical. As used herein, "spherical" refers to an aspect ratio of 1.0 to 1.5, preferably 1.0 to 1.4, and more preferably 1.0 to 1.3. Having such a shape, component of interest-containing hollow particles that are nuclear particles show good fluidity when they are tableted, or filled in capsule and the like, and the efficiency is also improved during processing such as coating and the like.

Component of interest-containing hollow particles that are nuclear particles are preferably those comprising 1 to 70% by weight of component of interest, 1 to 30% by weight of macromolecule, and 1 to 90% by weight of additive for the component of interest-containing hollow particles that are nuclear particles per 100% by weight of the component of interest-containing hollow particles that are nuclear particles.

Component of interest-containing hollow particles that are nuclear particles are more preferably those comprising 5 to 50% by weight of component of interest, 1 to 40% by weight of macromolecule, and 5 to 80% by weight of additive for the component of interest-containing hollow particles that are nuclear particles per 100% by weight of the component of interest-containing hollow particles that are nuclear particles.

Component of interest-containing hollow particles that are nuclear particles are still more preferably those comprising 10 to 40% by weight of component of interest, 10 to 40% by weight of macromolecule, and 10 to 70% by weight of additive for the component of interest-containing hollow particles that are nuclear particles per 100% by weight of the component of interest-containing hollow particles that are nuclear particles.

Component of interest-containing hollow particles that are nuclear particles are most preferably those comprising 15 to 30% by weight of component of interest, 10 to 30% by weight of macromolecule, and 20 to 60% by weight of additive for the component of interest-containing hollow particles that are nuclear particles per 100% by weight of the component of interest-containing hollow particles that are nuclear particles.

The mean particle size of macromolecules used as a raw material is generally 5-fold or greater, preferably 10-fold or greater, more preferably 15-fold or greater, still more preferably 20-fold or greater, and mots preferably 25-fold or greater than the mean particle size of components of interest and/or additive for the component of interest-containing hollow particles used as a raw material. The mean particle size is generally 1000-fold or less, preferably 500-fold or less, and more preferably 100-fold or less.

Furthermore, it is preferable that the particle size distribution of macromolecules used as a raw material does not overlap the particle size distribution of components of interest and/or additive for the component of interest-containing hollow particles used as a raw material. Specifically, cumulative 10% point of particle size D10 in for example volume based measurement of macromolecules is preferably greater than the cumulative 90% point of particle size D90 of components of interest and/or additive for the component of interest-containing hollow particles. In other words, cumulative 10% point of particle size D10 of macromolecules is preferably 1-fold or greater, more preferably 2-fold or greater, and still more preferably 4-fold or greater than the cumulative 90% point of particle size D90 of the component of interest and/or additive for the component of interest-containing hollow particles. The cumulative 10% point of particle size D10 is also generally 5000000-fold or less.

Component of interest-containing hollow particles that are nuclear particles are preferably those comprising 1 to 70% by weight of component of interest and 1 to 30% by weight of macromolecule (more preferably those comprising 5 to 50% by weight of component of interest and 1 to 40% by weight of macromolecule, still more preferably those comprising 10 to 40% by weight of component of interest and 10 to 40% by weight of macromolecule; and most preferably those comprising 15 to 30% by weight of component of interest and 10 to 30% by weight of macromolecule) per 100% by weight of the component of interest-containing hollow particles that are nuclear particles, and a "preferred mean particle size of macromolecules used as a raw material" which is generally 10-fold or greater (preferably 15-fold or greater, more preferably 25-fold or greater) than the mean particle size of the components of interest used as a raw material.

Component of interest-containing hollow particles that are nuclear particles are those comprising 1 to 70% by weight of component of interest, 1 to 30% by weight of macromolecule, and 1 to 90% by weight of additive for the component of interest-containing hollow particles (more preferably those comprising 5 to 50% by weight of component of interest, 1 to 40% by weight of macromolecule, and 5 to 80% by weight of additive for the component of interest-containing hollow particles, still more preferably those comprising 10 to 40% by weight of component of interest, 10 to 40% by weight of macromolecule, and 10 to 70% by weight of additive for the component of interest-containing hollow particles, and most preferably those comprising 15 to 30% by weight of component of interest, 10 to 30% by weight of macromolecule, and 20 to 60% by weight of additive for the component of interest-containing hollow particles) per 100% by weight of the component of interest-containing hollow particles that are nuclear particles, and a preferred mean particle size of macromolecules used as a raw material which is 10-fold or greater (preferably 15-fold or greater and more preferably 25-fold or greater) than the mean particle size of powder mix of the component of interest and another additive used as a raw material.

Manufacturing Method

The manufacturing method of particles coated with coatable microparticles of the invention comprises the (1) step of preparing an inner core comprising a component of interest and a macromolecule, and the (2) step of adding the coatable microparticles to the inner core, and coating the mixture while spraying a solvent that can dissolve the macromolecule. The manufacturing method of particles coated with coatable microparticles of the invention is a method that is simple yet has excellent coatability (coating time and coverage).

The (1) step of preparing an inner core comprising a component of interest and a macromolecule of the invention can be performed by loading a "macromolecule" and "component of interest" into a granulator as powder and granulating while spraying a predetermined amount of solvent under specific mixing/granulating conditions, resulting in nuclear particles in a wet powder state.

The (2) step of adding the coatable microparticles to the inner core, and coating the mixture while spraying a solvent that can dissolve the macromolecule of the invention can be performed by coating the nuclear particles in a wet powder state while spraying a solvent that can dissolve a predetermined amount of macromolecule under a specific coating condition. The resulting particles in a wet powder state can be dried by fluidized bed drying or the like.

A coating method can be appropriately selected from granulation methods having a function for rolling nuclear particles during coating. For example, particles can be manufactured using stirring granulation method, mixing stirring granulation method, high-speed stirring granulation method, high-speed mixing stirring granulation method, rolling and stirring fluidized bed granulation method, or rolling granulation method. In particular, it is preferable to use stirring granulation method, mixing stirring granulation method, high-speed stirring granulation method, or high-speed mixing stirring granulation method. Examples of granulators that are used for stirring granulation, mixing stirring granulation or the like include Intensive Mixer (Nippon Eirich), versatile mixer (Shinagawa Machinery Works), Super mixer (Kawata Mfg. Co., Ltd.), FM mixer (Nippon Coke & Engineering Co., Ltd.), SPG series (Fuji Paudal Co, Ltd.), Vertical Granulator (e.g., models FM-VG-05 and FM-VG-100, Powrex Corp), High-speed agitating mixer and granulator Pharma Matrix (Nara Machinery Co., Ltd.), high-speed mixer (FUKAE POWTEC Co, Ltd.), Granumeist (Freund Corporation), New-Gra Machine (Seishin Enterprise Co., Ltd.), Triple Master (Shinagawa Machinery Works), and the like. In the present invention, a simple fluidized bed granulation method is not preferable because the drying efficiency is too high such that coating would not progress.

As a drying method, a known method can be appropriately selected. Examples thereof include drying using a rack dryer or fluidized bed. Drying using a fluidized bed is preferable from the viewpoint of manufacturability.

Any mixing method can be appropriately selected, as long as the method has a mixing function. For example, a diffusion mixer such as a tumbler mixer, V blender, or W blender, or a convection mixer such as a ribbon mixer, Nauta mixer, or planetary mixer can be used.

Any tableting method can be appropriately selected, as long as the method has a function of compression molding a powder. Examples thereof include a tableting apparatus classified as a tablet press. A lubricant can also be added to the tablet of the invention by an external lubrication method.

As used herein, "solvent" refers to all acceptable solvents in the art for a drug, quasi-drug, cosmetic, food product, or the like. Solvent can be any solvent that can dissolve a macromolecule to be used. A pharmaceutically acceptable solvent is preferred from the viewpoint of using coated component of interest-containing hollow particles as a medicament. Such a solvent can be appropriately selected in accordance with the types of component of interest, macromolecule, or additive or the like. Several types of solvent can be mixed and used.

Examples of "solvent" in the present invention include water, alcohol based solvents (e.g., methanol, ethanol, n-propyl alcohol, isopropyl alcohol, 2-methoxyethanol, 2-ethoxyethanol, and other optionally substituted lower alkanol), ketone based solvents (e.g., acetone, methyl ethyl ketone, and other lower alkyl ketone), ester based solvents (e.g., ethyl acetate ester and other lower alkyl esters of acetic acid) and other mixture solvents.

Specifically, the present invention can use a solvent that can dissolve a macromolecule (e.g., water, hydroalcoholic solvent, or the like) as the solvent when using a water soluble macromolecule as the macromolecule. Water or hydrous ethanol can be especially preferably used. The present invention can also use a solvent that can dissolve a macromolecule (e.g., alcohol based solvent, ketone based solvent, ester based solvent, or the like) as the solvent when using a water insoluble macromolecule as the macromolecule. The present invention can use a solvent that can dissolve each of the macromolecules including enteric macromolecule, stomach soluble macromolecule, and chitosan (e.g., alcohol based solvent, more specifically ethanol) as the solvent.

While the amount of solvent used in the present invention varies by the type and amount of macromolecule or the like, the amount is generally 5 to 60% by weight, preferably 10 to 53% by weight, more preferably 10 to 40% by weight, and still more preferably 15 to 40% by weight per 100% by weight of the total amount of each component constituting a particle. The solvent is preferably added to a powder mixture comprising a component of interest and a macromolecule by spraying.

A solvent in the present invention can be sprayed using a spray gun that is generally used for granulation. Specific examples thereof include a needle spray gun (Tomita engineering Co., Ltd.) and the like. To enhance the granulation yield, it is preferable to spray a solvent as little as possible to parts other than the powder within the granulation container, i.e., to the inner wall of the granulation container or the like, and to spray a solvent in as broad of a range of powder within the granulation container as possible.

When using an additive for coated component of interest-containing hollow particles, the mean particle size of mixed powder of a component of interest and additive for coated component of interest-containing hollow particles used as a raw material is important for the manufacture of coated component of interest-containing hollow particles. In such a case, the mean particle size of a macromolecule used as a raw material is preferably 5-fold or greater, preferably 10-fold or greater, more preferably 15-fold or greater, and especially preferably 25-fold or greater than the mean particle size of mixed powder of a component of interest and additive for coated component of interest-containing hollow particles used as a raw material. The mean particle size is generally 1000-fold or less, preferably 500-fold or less, and more preferably 100-fold or less.

Furthermore, the particle size distribution of macromolecules used as a raw material preferably does not overlap with the particle size distribution of mixed powder of a component of interest and additive for coated component of interest-containing hollow particles used as a raw material. Specifically, cumulative 10% point of particle size D10 in for example volume base measurement of macromolecules used as a raw material is preferably greater than the cumulative 90% point of particle size D90 of mixed powder of a component of interest and additive for coated component of interest-containing hollow particles used as a raw material. In other words, cumulative 10% point of particle size D10 of macromolecules used as a raw material is preferably 1-fold or greater (i.e., granulation distribution ratio of macromolecule and component of interest (D10/D90) is 1-fold or greater), more preferably 2-fold or greater, and still more preferably 4-fold or greater than the cumulative 90% point of particle size D90 of the component of interest and additive for the component of interest-containing hollow particles used as a raw material. The cumulative 10% point of particle size D10 is also generally 500 or less, preferably 250-fold or less, and more preferably 50-fold or less.

Cumulative 50% point of particle size D50 in volume base measurement of macromolecules used as a raw material is preferably greater than the cumulative 50% point of particle size D50 of mixed powder of a component of interest and additive for coated component of interest-containing hollow particles used as a raw material. In other words, cumulative 50% point of particle size D50 of macromolecules used as a raw material is preferably 1-fold or greater (i.e., granulation distribution ratio of macromolecule and component of interest (D50/D50) is 1-fold or greater), more preferably 2-fold or greater, and still more preferably 4-fold or greater than the cumulative 50% point of particle size D50 of mixed powder of the component of interest and additive for the component of interest-containing hollow particles used as a raw material. The cumulative 50% point of particle size D50 is also generally 500-fold or less, preferably 250-fold or less, and more preferably 50-fold or less.

The "aspect ratio" in the present invention is a ratio of the minor diameter and the major diameter of a particle, and is an indication of the sphericity. The aspect ratio can be determined by calculation by, for example, the following formula.

$$\text{Aspect ratio} = \text{major diameter of particle}/\text{minor diameter of particle}$$

The major diameter and minor diameter of the particle are non-destructively measured by a benchtop micro-CT (manufactured by SKYSCAN, SKYSCAN1172), and the average of 10 measurements is used.

In addition, Millitrac JPA (NIKKISO CO., LTD.) may be used for the measurement

The "particle size distribution width" in the present invention can be obtained from the ratio of cumulative 90% particle size D90 and cumulative 10% particle size D10 (D90/D10) in the volume based measurement of a powder particle. The particle size distribution of the coated component of interest-containing hollow particles can be conveniently adjusted by adjusting the particle size of the macromolecule and, for example, a particle group having a narrow particle size distribution width can be produced. Such particle size distribution width is measured by a laser diffraction particle size analyzer (manufactured by POWREX CORPORATION, Particle Viewer) by volume basis.

In the present invention, "width of particle size distribution is narrow" means that a specific particle size distribution width (D90/D10) is not more than 6.0, preferably not more than 5.0, more preferably not more than 4.0, further preferably not more than 3.0.

The strength of hollow particles can be evaluated by particle shell strength. The "particle shell strength" in the present invention can be obtained by calculation by the following formula.

$$\text{Particle shell strength [MPa]} = 2.8P/(\pi \times d^2 - \pi \times d'^2) \times 1000$$

P: destructive testing force of particles [mN], d: diameter of coated component of interest-containing hollow particles [μm], d': diameter of hollow section [μm]

Such a destructive test force of particles and the diameter of coated component of interest-containing hollow particles are measured by SHIMADZU Corporation microcompression testing machine MCT-W500 (manufactured by Shimadzu Corporation).

A "diameter of a hollow section" in the present invention can be obtained by calculation by the following formula.

$$\text{Diameter of hollow section [μm]} = (\text{major diameter of hollow section} + \text{minor diameter of hollow section})/2$$

The major diameter and minor diameter of the hollow of the particle are non-destructively measured by a benchtop micro-CT (manufactured by SKYSCAN, SKYSCAN1172) and the average of 10 measurements is used.

In the present invention, component of interest-containing hollow particles that are nuclear (see "MEDICAMENT-CONTAINING HOLLOW PARTICLE" described in WO 2014/030656 for a representative example) is desired to have a sufficient particle strength, so that it will be efficiently coated without being broken or chipped, even when it is coated with a functional macromolecule and the like to impart an additional function by using a fluidized-bed granulator or various particulate coating machine and the like that require further mechanical strength of particles, and maintain the hollow without being crushed even after compression. When a component of interest is a drug, such particles are referred to as drug-containing hollow particles. Such particles are similarly referred by such an alternate name when using a component of a food product or other components.

Coated component of interest-containing hollow particles have sufficient particle strength. Since the coated component of interest-containing hollow particles have a hollow section, a conventional particle strength measurement method cannot perform an accurate evaluation since it also calculates the hollow as a solid. Thus, the measurement is possible by the particle shell strength excluding the hollow. The "sufficient particle strength" in the present invention specifically means that the particle shell strength of the medicament-containing particle is not less than 2.0 MPa, preferably not less than 3.0 MPa, more preferably not less than 4.0 MPa, further preferably not less than 5.0 MPa.

"Particle size of coated component of interest-containing hollow particles" in the present invention can be obtained by calculation by the following formula.

Particle size of coated component of interest-containing hollow particles in the present invention is found by calculating the following equation.

Particle size of coated component of interest-containing hollow particles [μm]=(major diameter of particle+minor diameter of particle)/2

The major diameter and minor diameter of the particle are non-destructively measured by a benchtop micro-CT (manufactured by SKYSCAN, SKYSCAN1172) and the average of 10 measurements is used.

The "shell thickness" in the present invention can be obtained by calculation by the following formula.

Shell thickness [μm]=(particle size of coated component of interest-containing hollow particles diameter of hollow section)/2

The particle size of coated component of interest-containing hollow particles and the diameter of hollow section are non-destructively measured by a desktop micro-CT scanner (manufactured by SKYSCAN, SKYSCAN1172) and the average of 10 measurements is used.

"Percentage of Shell thickness" in the present invention can be obtained by calculation by the following formula.

Percentage of Shell thickness [%]=(shell thickness/ (particle size of component of interest-containing hollow particles/2))×100

The particle size of component of interest-containing hollow particles is non-destructively measured by a benchtop micro-CT (manufactured by SKYSCAN, SKYSCAN1172) and the average of 10 measurements is used.

"Volume ratio of a hollow section" in the present invention can be obtained by calculation by the following formula.

Volume ratio of a hollow section [%]=(4/3×π×(diameter of hollow section/2)$^3$)/(4/3×π×(particle size of component of interest-containing hollow particles/2)$^3$)×100

The particle size of coated component of interest-containing hollow particles and the diameter of a hollow section are non-destructively measured by a benchtop micro-CT (manufactured by SKYSCAN, SKYSCAN1172) and the average of 10 measurements is used.

The "particle size distribution ratio (D50/D50) of macromolecules and medicament" in the present invention can be obtained by calculation by the following formula.

Particle size distribution ratio of macromolecules and components of interest(D50/D50)=D50 of macromolecules/D50 of components of interest The "particle size distribution ratio (D50/D50) of macromolecules and mixed powder of components of interest and other additives" in the present invention can be obtained by calculation by the following formula.

Particle size distribution ratio of macromolecules and mixed powder of mixed powder of components of interest and other additives (D50/D50)=D50 of macromolecules/D50 of mixed powder of mixed powder of components of interest and other additives The particle size distribution of macromolecules, components of interest, and mixed powder of components of interest and other additives is measured by a laser diffraction particle size analyzer (manufactured by POWREX CORPORATION, Particle Viewer) or a laser diffraction particle size analyzer (manufactured by Shimadzu Corporation, SALD-3000) or SYMPATEC, HELOS & RODOS) by volume basis.

The "particle size distribution ratio (D10/D90) of macromolecules and components of interest (D10/D90)" in the present invention can be obtained by calculation by the following formula.

particle size distribution ratio of macromolecules and components of interest(D10/D90)=D10 of macromolecules/D90 of components of interest The "particle size distribution ratio (D10/D90) of macromolecules and mixed powder of components of interest and other additives" in the present invention can be obtained by calculation by the following formula.

Particle size distribution ratio (D10/D90) of macromolecules and mixed powder of mixed powder of components of interest and other additives=D10 of macromolecules/D90 of mixed powder of mixed powder of components of interest and other additives The particle size distribution of macromolecules, components of interest, and mixed powder of components of interest and other additives is measured by a laser diffraction particle size analyzer (manufactured by POWREX CORPORATION, Particle Viewer) or a laser diffraction particle size analyzer (manufactured by Shimadzu Corporation, SALD-3000) or SYMPATEC, HELOS & RODOS) by volume basis.

The present invention also relates to a manufacturing method of coated component of interest-containing hollow particles, comprising granulating while spraying a solvent that can dissolve a macromolecule to a powder mixture comprising a component of interest and a macromolecule, and coated component of interest-containing hollow particles manufactured by said method.

Examples of the component of interest, macromolecule, and solvent that can dissolve a macromolecule include the same ones as those discussed with regard to the manufacturing method of coated component of interest-containing hollow particles. Another additive can be included as needed in said method. Examples of other additives include the same ones discussed with regard to the manufacturing method of coated component of interest-containing hollow particles.

Examples of the granulating method, drying method, spraying method of solvent and the like include the same ones as those discussed with regard to the manufacturing method of coated component of interest-containing hollow particles.

While a conventional method, i.e., a method using a fluidized bed granulator, requires several days or more as the coating time, the coating time is 1 hour or less when using the manufacturing method of the invention. Since coating requires a short period of time, production efficiency is enhanced.

For coated component of interest-containing hollow particles, the function of a macromolecule contained in nuclear particles can be controlled by controlling the amount of coating, regardless of the type of coating microparticle. For example, if a macromolecule with a sustained release property is used for nuclear particles, coated component of interest-containing hollow particles having any sustained release profile (any 50% dissolution time) can be manufactured by controlling the amount of coating. Similarly, by using a macromolecule having enteric, stomach soluble, or bitterness masking property for nuclear particles, these functions can be controlled in any manner.

Degradation of a component of interest contained in nuclear particles by light can be suppressed by selecting microparticles with a photostable function as the coating microparticles. Examples of microparticles with a photostable function include titanium oxide, Red Ferric Oxide, Yellow Ferric Oxide, black iron oxide, pigment, and the like.

(3) Pharmaceutical Composition and Application Thereof

The present invention relates to a pharmaceutical composition, therapeutic agent, and/or prophylactic agent for treating and/or preventing a digestive system disease or digestive system symptom, comprising coated component of interest-containing hollow particles comprising a component of interest of the invention. Preferably, the digestive system disease is a constipation-predominant irritable bowel syndrome (IBS) or chronic constipation. Preferred examples of coated, component of interest-containing hollow particles comprising a drug of the invention include the aforementioned (v) coated component of interest-containing hollow particles. Preferred examples of the pharmaceutical composition, therapeutic agent, and/or prophylactic agent include formulations comprising the aforementioned (2) coated component of interest-containing hollow particles.

In the present invention, "prevention (prophylactic)" is an act of administering the component of interest of the invention, which is the active ingredient, to a healthy individual who has not developed a disease or is in an unhealthy condition as of the administration. "Prophylactic agent" is administered to such a healthy individual. For example, a prophylactic agent is intended to prevent the development of a disease and is expected to be suitable for especially individuals who have had a symptom of a disease previously or individuals considered to have increased risk of suffering from the disease. "Therapy" is an act of administering the component of interest, which is an active ingredient, to an individual (patient) diagnosed to have developed a disease by a physician. "Therapeutic agent" is administered to such a patient. For example, a therapeutic agent is intended to alleviate a disease or symptom, prevent exacerbation of a disease or symptom, or restore the condition to that prior to developing the disease. Even when the objective of administration is prevention of exacerbation of a disease or symptom, this is an act of therapy if the agent is administered to a patient.

In the present invention, specific examples of "digestive system disease or digestive system symptom" include the diseases or symptoms of the following (i) to (iii).
(i) digestive system diseases, such as irritable bowel syndrome, atonic constipation, habitual constipation, chronic constipation, constipation induced by drugs such as morphine and antipsychotics, constipation accompanied by Parkinson's disease, constipation accompanying multiple sclerosis, constipation accompanying diabetes, and constipation or defecation disorder due to a contrast agent (as an endoscopic examination or pretreatment for barium intestinal enema X-ray examination);
(ii) digestive system diseases such as functional dyspepsia, acute/chronic gastritis, reflux esophagitis, gastric ulcer, duodenal ulcer, gastric neurosis, postoperative paralytic ileus, senile ileus, non-diffuse gastroesophageal reflux disease, NSAID ulcer, diabetic gastroparesis, post-gastrectomy syndrome, and intestinal pseudo-obstruction; and
(iii) digestive system diseases such as the digestive system diseases described in (i) and (ii), scleroderma, diabetes, anorexia in esophagus/biliary tract disease, nausea, vomiting, bloating, epigastric discomfort, abdominal pain, heartburn, and eructation.

The dosage form of the component of interest of the invention can be either oral administration or parenteral administration. The dosage varies by the dosing method, symptom of patient, age, or the like, but is generally in the range of 0.01 to 30 mg/kg/day, preferably 0.05 to 10 mg/kg/day, and more preferably 0.1 to 3 mg/kg/day. Another preferred embodiment of the dosage is generally in a range of 0.01 mg to 1000 mg/day, preferably 0.1 mg to 500 mg/day, more preferably 0.5 mg to 300 mg/day, still more preferably 1 mg to 200 mg/day, and most preferably 5 mg to 100 mg/day. The number of daily doses is one or several per day, such as 1, 2, or 3 doses given each time.

Examples of the dosage form of an oral formulation include granules, tablets, capsules, suspension (aqueous suspension, oil suspension), emulsion, and the like. Examples of parenteral formulations include injection, intravenous drip agent, suppository (intrarectally administered agent), nasal agent, sublingual agent, transdermally absorbed agent [lotion, emulsion, ointment, cream, jelly, gel, patch (tape, transdermal patch formulation, poultice, and the like), externally applied powder, and the like], and the like.

Preferably, the component of interest of the invention is orally administered as coated component of interest-containing hollow particles or formulation of the invention. More preferable examples of the dosage form of oral formulation include tablets, as described in the aforementioned (2) formulation comprising coated component of interest-containing hollow particles. Examples of more preferred examples of tablets include orally disintegrating tablets.

This includes combined therapy that administers the compound or pharmaceutically acceptable salt thereof, or hydrate or solvate thereof, or coated component of interest-containing hollow particles, formulation, or pharmaceutical composition of the invention in combination with one or more of the following other agents sequentially or simultaneously.

For digestive system diseases accompanying constipation, specific examples include saline laxatives such as magnesium sulfate, magnesium oxide, and magnesium citrate, invasive laxatives such as dioctyl sodium, sulfosuccinate, and casanthranol, bulk-forming laxatives such as carmellose, intestine irritating laxatives such as bisacodyl, picosulfate, senna, and sennoside, small intestine irritating laxatives such as castor oil, bowel cleansing agents such as Magcorol and Niflec, and the like.

For digestive system diseases such as functional dyspepsia, acute/chronic gastritis, reflux esophagitis, non-diffuse gastroesophageal reflux disease, diabetic gastroparesis, gastric ulcer, duodenal ulcer, NSAID ulcer, gastric neurosis, postoperative paralytic ileus, senile ileus, post-gastrectomy syndrome, and intestinal pseudo-obstruction, examples thereof include proton pump inhibitors such as omeprazole, rabeprazole, and lansoprazole, antacids such as histamine $H_2$ receptor inhibitors such as famotidine, ranitidine, and cimetidine, gastrointestinal function regulators such as Mosapride and domperidone, gastric mucosa protective agents, intestinal regulators, and the like.

EXAMPLES

The present invention is specifically described in more detail with Examples, Test Examples, and Comparative Examples, but the present invention is not limited thereto. The present invention can also be modified to the extent that the modified invention remains within the scope of the present invention. The compound names denoted in the following Examples, Test Examples, and Comparative Examples do not necessarily follow the IUPAC nomenclature.

Unless specifically noted otherwise, % in solvent indicates (W/W %) and % in particles indicate % by weight in the Examples, Test Examples, and Comparative Examples.

The following components were used in the Examples and Comparative Examples, unless specifically noted otherwise.

Aminoalkyl methacrylate copolymer RS (Eudragit RSPO): Evonik Degussa Japan Co., Ltd.

Dried methacrylic acid copolymer LD (Eudragit L100-55): Evonik Degussa Japan Co., Ltd.

Aminoalkyl methacrylate copolymer E (Eudragit E 100): Evonik Degussa Japan Co., Ltd.

Hydroxypropyl cellulose (HPC-L): Nippon Soda Co., Ltd.

Hydrogenated castor oil (Lubriwax-101): Freund Corporation

Talc (NANO ACE® D-1000): Nippon Talc, Co., Ltd.
Talc (Micro Ace® P-3): Nippon Talc, Co., Ltd.
Talc (High grade talc MSP): Nippon Talc, Co., Ltd.
Talc (Sodium bicarbonate talc H): Nippon Talc, Co., Ltd.

Crystalline cellulose (Ceolus PH-F20JP) Asahi Kasei Chemicals Corporation

Crystalline cellulose (Ceolus PH-101) Asahi Kasei Chemicals Corporation

Crystalline cellulose (Ceolus UF-702) Asahi Kasei Chemicals Corporation

Crystalline cellulose (Ceolus KG-1000) Asahi Kasei Chemicals Corporation

PEARLITOL FLASH (D-mannitol 80% corn starch 20% premix product): Roquette Japan K.K.

Corn starch (Corn starch XX16): Nihon Shokuhin Kako Co., Ltd.

Alginic acid (Alginic acid G): Kimica Corporation
Red Ferric Oxide (Red Ferric Oxide S): Kishi Kasei
Yellow Ferric Oxide (Yellow Ferric Oxide): San-Ei Gen F.F.I., Inc.

Titanium oxide (Titanium oxide (NA61): Toho Titanium Co., Ltd.

Magnesium stearate (Magnesium stearate): Taihei Chemical Industrial Co., Ltd.

D-mannitol (NONPAREIL-108 200): Freund Corporation
D-mannitol (PEARLITOL 25 C): Roquette Japan K.K.
D-mannitol (PEARLITOL 200 SD): Roquette Japan K.K.

<Testing Method>

The testing methods in the Examples, Test Examples, and Comparative Examples are the following.

(Particle Size Distribution)

The particle size distribution of components of interest, macromolecules, other additives, mixed powder of components of interest and other additives, resulting coated component of interest-containing hollow particles, and coatable microparticles was measured based on volume with a laser diffraction particle size distribution analyzer (e.g., Powrex Corp: PARTICLE VIEWER or SYMPATEC: HELOS & RODOS).

(Appearance of Coated Component of Interest-Containing Hollow Particles)

The appearance of particles was observed with a scanning electron microscope (Hitachi, Ltd., model S-3400N).

(Microscope Raman Imaging of the Cross-Section of Coated Component of Interest-Containing Hollow Particles)

The cross-section of particles was measured with a micro-Raman imaging system (HORIBA Jobin Yvon GmbH, LabRAM ARAMIS).

<Active Pharmaceutical Ingredient>

The following were used as the active pharmaceutical ingredients in the Examples, Test Examples, and Comparative Examples, unless specifically noted otherwise.

Zonisamide (1,2-BENZISOXAZOLE-3-METHANE-SULFONAMIDE; hereinafter compound A)

Nifedipine (3,5-DIMETHYL2,6-DIMETHYL-4-(2-NITROPHENYL)-1,4-DIHYDROPYRIDINE-3,5-DICARBOXYLATE; hereinafter compound B)

N-ETHYL-7,8-DIHYDRO-7-METHYL-8-OXO-2-PHENYL-N-(PHENYLMETHYL)-9H-PURINE-9-ACETAMIDE (compound C)

(S)-4-AMINO-5-CHLORO-N-[{4-[(1-HYDROXY-ACETYL-4-PIPERIDINYL)METHYL]-2-MORPHOLINYL}METHYL]-2-METHOXYBENZ-AMIDE (compound D)

Acetaminophen (N-(4-HYDROXYPHENYL)ACETAMIDE; hereinafter compound E)

Anhydrous caffeine (1,3,7-TRIMETHYLPURINE-2,6-DIONE; hereinafter compound F)

Haloperidol (4-[4-(4-CHLOROPHENYL)-4-HYDROXY-1-PIPERIDYL]-1-(4-FLUOROPHENYL)-BUTAN-1-ONE; hereinafter compound G)

Example 1

Manufacture of Coated Component of Interest-Containing Hollow Particles with Different Amounts of Coating Coated component of interest-containing hollow particles of the invention with different amounts of coating were manufactured in Examples 1-1 to 1-3. For the amount of coating, 5% by weight, 10% by weight, and 20% by weight were selected as shown in Table 1. First, nuclear particles for coating were manufactured in accordance with Table 1. Specifically, aminoalkyl methacrylate copolymer RS and compound A were loaded into a high-speed stirring granulator, i.e., Vertical Granulator (model FM-VG-05, capacity: 5 L, Powrex Corp) at the amounts described in Table 1 as powder. Granulation was then performed while spraying a predetermined amount of aqueous 95% ethanol solution under the mixing/granulation conditions shown in Table 2-1 to obtain nuclear particles for coating in a wet powder state. Subsequent to the above step, 5, 10, and 20% by weight, with respect to the loaded amount, of talc (Micro Ace® P-3), which is an additive for coating, was loaded into a high-speed stirring granulator containing the nuclear particles as powder. The particles and powder were rolled under the coating granulation conditions shown in Table 2-1 for coating granulation while spraying a predetermined amount of aqueous 95% ethanol solution. The coated component of interest-containing hollow particles in a wet powder state were then subjected to fluidized bed drying using a Multiplex model MP-01 (Powrex Corp) to obtain the coated component of interest-containing hollow particles in Examples 1-1 to 1-3. Table 13 shows the coating time and the time that was required for the manufacture of the resulting particles. The appearance of the particles obtained in Example 1-1 is shown in FIG. 2. FIG. 17 shows the results of microscope Raman imaging for the particles obtained in Example 1-3. FIG. 17 shows that components of interest are contained in particles, and talc of coating microparticles is coating the particle surface.

<Raman Imaging Conditions>
Laser wavelength: 633 nm
Grating: 600
Objective lens: 50 times magnification
Cumulative number: 2 times
Cumulative time: 5 seconds Comparative Example 1

Manufacture of Nuclear Particles for Coating

In Comparative Example 1, only particles that were not coated, i.e., nuclear particles for coating, were manufactured

TABLE 1

Table 1 formulation of Comparative Example 1 and Examples 1-1 to 1-3

| | Comparative Example 1 | | Example 1-1 | | Example 1-2 | | Example 1-3 | |
|---|---|---|---|---|---|---|---|---|
| | Amount loaded (g) | Formulation ratio (%) | Amount loaded (g) | Formulation ratio (%) | Amount loaded (g) | Formulation ratio (%) | Amount loaded (g) | Formulation ratio (5) |
| Compound A (ground product of JM) | 560 | 80 | 525 | 75 | 490 | 70 | 420 | 60 |
| Aminoalkyl methacrylate copolymer RS (No. 100 on) | 140 | 20 | 140 | 20 | 140 | 20 | 140 | 20 |
| Talc (Micro Ace ® P-3) | — | — | 35 | 5 | 70 | 10 | 140 | 20 |
| (Aqueous 95% ethanol solution) (manufacture of nuclear particles) | (127) | (18) | (200) | (29) | (270) | (39) | (180) | (26) |
| (Aqueous 95% ethanol solution) (manufacture of coated particles) | — | — | (7) | (1) | (28) | (4) | (30) | (4) |
| Total | 700 | 100 | 700 | 100 | 700 | 100 | 700 | 100 |

TABLE 2-1

Manufacturing conditions of Comparative Example 1 and Examples 1-1 to 1-3

| Premixing step | Equipment name | Mixing time | No. of blade rotations | No. of chopper rotations | | |
|---|---|---|---|---|---|---|
| | Vertical Granulator (FM-VG-05, Powrex Corp) | 3 min | 400 min$^{-1}$ | 3000 min$^{-1}$ | — | |
| Granulation step | Equipment name | No. of blade rotations | No. of chopper rotations | Solvent addition method | Solvent adding rate | |
| | Vertical Granulator (FM-VG-05, Powrex Corp)) | 400 min$^{-1}$ | 3000 min$^{-1}$ | Spray addition | 8 g/min | |
| Coating step | Equipment name | No. of blade rotations | No. of chopper rotations | Solvent addition method | Solvent adding rate | |
| | Vertical Granulator (FM-VG-05, Powrex Corp) | 400 min$^{-1}$ | 3000 min$^{-1}$ | Spray addition | 8 g/min | |
| | Vertical Granulator (FM-VG-01, Powrex Corp) | 520 min$^{-1}$ | 3000 min$^{-1}$ | Spray addition | 4 g/min | |
| Drying step | Equipment name | Temperature of supplied air | Amount of air supplied | Exhaust temperature after completion of drying | — | |
| | Multiplex (MP-01, Powrex Corp) | 80° C. | 0.5 m$^3$/min | 35° C. | — | | in accordance with the formulation ratio and amount loaded described in Table 1 in the same manner as Example 1. After granulating nuclear particles for coating in a wet powder state as in Example 1, the nuclear particles for coating in a wet powder state were subjected to fluidized bed drying using a Multiplex model MP-01 (Powrex Corp) to obtain the nuclear particles for coating of Comparative Example 1. The appearance of the particles obtained is shown in FIG. 1. FIG. 18 shows the results of microscope Raman imaging for the particles obtained in Comparative Example 1. FIG. 18 shows that components of interest are contained in the particles. The particle sizes of nuclear particles, component of interest, macromolecule, and additive used in Comparative Example 1 and Example 1 are shown in Table 2-2.

Example 2

Manufacture of Tablets Comprising Coated Component of Interest-Containing Hollow Particles with Different Amounts of Coating The tablets of Examples 2-1 to 2-3 were manufactured by weighing an additive, mixing, and tableting in accordance with the formulation ratio and amount loaded in Table 3 using the particles obtained in Examples 1-1 to 1-3. Table shows the coating time and time that was required for manufacture of the resulting particles.

Specifically, the ingredients were weighed in accordance with Table 3 and manually mixed using a plastic bag. The resulting mixed powder was tableted with a tabletop press TB-20H (NPA System) (round tablet Φ9.0 MM, 26 mg, tableting pressure: 6 KN).

TABLE 3

Tablet formulations of Comparative Example 2 and Examples 2-1 to 2-3

|  |  | Comparative Example 2 | | Example 2-1 | | Example 2-2 | | Example 2-3 | |
| --- | --- | --- | --- | --- | --- | --- | --- | --- | --- |
|  |  | Amount loaded (g) | Formulation ratio (%) | Amount loaded (g) | Formulation ratio (%) | Amount loaded (g) | Formulation ratio (%) | Amount loaded (g) | Formulation ratio (%) |
| Drug-containing hollow particles | Compound A (ground product of JM) | 2.504 | 38.4 | 50.025 | 38.5 | 50.05 | 38.5 | 50.04 | 38.5 |
|  | Aminoalkyl methacrylate copolymer RS (No. 100 on) | 0.626 | 9.6 | 13.34 | 10.3 | 14.3 | 11.0 | 16.68 | 12.8 |
|  | Talc (Micro Ace ® P-3) | — | — | 3.335 | 2.6 | 7.15 | 5.5 | 16.68 | 12.8 |
| Outer layer tablet component | D-mannitol (PEARLITOL 200 SD) | 2.34 | 36.0 | 49.7 | 38.2 | 44.9 | 34.5 | 33 | 25.4 |
|  | Crystalline cellulose (Coolus PH-101 | 0.98 | 15.0 | 13 | 10.0 | 13 | 10.0 | 13 | 10.0 |
|  | Magnesium stearate | 0.07 | 1.0 | 0.7 | 0.5 | 0.7 | 0.5 | 0.7 | 0.5 |
| Total |  | 6.52 | 100 | 130.1 | 100 | 130.1 | 100 | 130.1 | 100 |

<Raman Imaging Conditions>

Laser wavelength: 633 nm

Grating: 300

Objective lens: 20 times magnification

Cumulative number: 1 time

Cumulative time: 5 seconds

TABLE 2-2

Particle sizes of Comparative Example 1, compound A, aminoalkyl methacrylate copolymer RS (No. 100 on), and talc

|  | D10 | D50 | D90 |
| --- | --- | --- | --- |
| Comparative Example 1 | 94.1 | 248.9 | 290.0 |
| Compound A (ground product of JM) | 0.73 | 1.99 | 5.16 |
| Aminoalkyl methacrylate copolymer RS (No. 100 on) | 94.1 | 181.5 | 290.0 |
| Talc (Micro Ace P-3) | 1.0 | 3.5 | 8.3 |

Comparative Example 2

Manufacture of Tablets Comprising Nuclear Particles for Coating

Comparative Example 2, which is a tablet comprising the nuclear particles for coating manufactured in Comparative Example 1, was manufactured by weighing an additive, mixing, and tableting in accordance with the formulation ratio and amount loaded in Table 3 in the same manner as Example 2.

Test Example 1

Dissolution Test on Tablets Comprising Coated Component of Interest-Containing Hollow Particles with Different Amounts of Coating Dissolution tests were conducted using the tablets manufactured in Comparative Example 2 and Example 2. Water of 37° C./900 ML was used as the test solution for measurement at a number of rotations of 50 RPM based on the paddle method of a dissolution test method in the revised 16th Japanese Pharmacopoeia. The measurement times were 10, 15, 30, 45, 60, 90, 120, 360, 720, 1080, and 1440. The sampling solution was filtered and measured by HPLC to calculate the dissolution rate.

<HPLC Measurement Conditions>
Detector: ultraviolet visible spectrophotometer
Measurement wavelength: 285 NM
Column: WATERS ACQUITY UPLC C18 [2.1 MM Φ×30 MM]
Colum temperature: 40° C.
Amount of flow: 0.5 ML/MIN
Amount injected: 5 ML
Sample cooler: 25° C.
Syringe cleansing solution: water/acetonitrile mixture=1/1
Mobile phase: water/acetonitrile mixture=4/1

FIG. 3 shows the results of dissolution test on tablets obtained in Comparative Example 2 and Examples 2-1 to 2-3, and Table 13 shows the ratio of 50% dissolution times before and after coating. Dissolution time was extended by a factor of 4 or more. The ability to control release of particles increased with the increase in the amount of coating.

Example 4

Manufacture of Coated Component of Interest-Containing Hollow Particles Using Coatable Microparticles, with the Only Difference in Particle Sizes The coated component of interest-containing hollow particles of the invention with different coatable microparticle sizes were manufactured in Example 4.

As the coatable microparticles with different particle sizes, talc (NANO ACE® D-1000, median size of about 1 μM), talc (Micro Ace® P-3, median size of about 5 μM), talc (high-grade talc MSP, median size of about 12 μM), and talc (sodium bicarbonate talc H, median size of about 20 μM) were used.

Examples 4-1 to 4-3 were manufactured by the same method as Example 1 in accordance with the formulation ratio and amount described in Table 5. Specifically, compound A and granularity controlled product of aminoalkyl methacrylate copolymer RS (No. 100 ON fraction) were loaded into a high speed stirring granulator (model FM-VG-05, capacity: 5 L, Powrex Corp) and granulated while spraying a predetermined amount of aqueous 95% ethanol solution under the mixing and granulating conditions shown in Tablet 5 to obtain nuclear particles in a wet powder state. Subsequent to the above step, coatable microparticles, i.e., talc (NANO ACE® D-1000), talc (Micro Ace® P-3), talc (high-grade talc MSP), and talc (sodium bicarbonate talc H), were loaded into a high speed stirring granulator containing the nuclear particles in accordance with Table 5. Coating granulation was performed while spraying a predetermined amount of aqueous 95% ethanol solution under the coating granulation conditions shown in Table 2-1. The resulting particles were then subjected to fluidized bed drying using Multiplex model MP-01 (Powrex Corp) to obtain the coated component of interest-containing hollow particles of Examples 4-1 to 4-3.

TABLE 5

| | Example 4-1 | | Example 1-3 | | Example 4-2 | | Example 4-3 | |
|---|---|---|---|---|---|---|---|---|
| | Amount loaded (g) | Formulation ratio (%) | Amount loaded (g) | Formulation ratio (%) | Amount loaded (g) | Formulation ratio (%) | Amount loaded (g) | Formulation ratio (%) |
| Compound A (ground product of JM) | 360 | 64 | 420 | 60 | 288.3 | 64 | 560 | 64 |
| Aminoalkyl methacrylate copolymer RS (No. 100 on) | 90 | 16 | 140 | 20 | 72.1 | 16 | 140 | 16 |
| Talc (NANO ACE ® D-1000) | 112 | 20 | — | — | — | — | — | — |
| Talc (Micro Ace ® P-3) | — | — | 140 | 20 | — | — | — | — |
| Talc (high-grade talc MSP) | — | — | — | — | 89.6 | 20 | — | — |
| Talc (sodium bicarbonate talc H) | — | — | — | — | — | — | 175 | 20 |
| (Aqueous 95% ethanol solution) (manufacture of nuclear particles) | (106) | (37) | (100) | (26) | (09) | (10) | (220) | (25) |
| (Aqueous 95% ethanol solution) (manufacture of coated particles) | (190) | (34) | (30) | (4) | (100) | (22) | (48) | (5) |
| total | 562 | 100 | 700 | 100 | 450 | 100 | 875 | 100 |

Test Example 3

Dissolution Test on Coated Component of Interest-Containing Hollow Particles with Different Particle Size Coatable Microparticles A dissolution test was conducted using the particles manufactured in Example 4 and particles manufactured in Comparative Example 1. The list of tested formulations is shown in Table 6. The test conditions were the same as Test Example 1. The results are shown in FIG. 4. Table 13 shows the coating rate, coating time, and the time that was required for the manufacture of the resulting particles.

Table 13 shows the ratio of 50% dissolution times before and after coating for the coated component of interest-containing hollow particles using coatable microparticles of all particle sizes. The dissolution time was extended by a factor of 19 or greater, resulting in an effect of suppressing the release rate.

The particles size, water solubility, wettability, and swellability of the particles used are shown in Table 7.

Examples 5-1 to 5-5 were manufactured by the same method as Example 1 in accordance with the formulation rate and amount loaded described in Table 8. Specifically, compound A and granularity controlled product of aminoalkyl methacrylate copolymer RS (No. 100 ON fraction) were loaded into a high speed stirring granulator (model FM-VG-05, capacity: 5 L, Powrex Corp) and granulated while spraying a predetermined amount of aqueous 95% ethanol solution under the mixing and granulating conditions shown in Table 2-1 to obtain nuclear particles in a wet powder state. Subsequent to the above step, coatable microparticles, i.e., hydrogenated oil, magnesium stearate, sodium stearyl fumarate, titanium oxide, or crystalline cellulose (Ceolus PH-F20JP), were loaded into a high speed stirring granulator containing the nuclear particles in accordance with Table 8. Coating degranulation was performed while spraying a predetermined amount of aqueous 95% ethanol solution under the coating granulation conditions shown in Table 2-1. The resulting particles were then subjected to fluidized bed drying using Multiplex model MP-01 (Powrex Corp) to obtain the coated component of interest-containing hollow particles of Examples 5-1 to 5-5. Table 13 shows the coating rate, coating time, and the time that was required for the manufacture of the resulting particles.

TABLE 6

Samples tested in Test Example 3

| | | Comparative Example 1 | | Example 4-1 | | Example 4-2 | | Example 4-3 | |
|---|---|---|---|---|---|---|---|---|---|
| | | Amount loaded (g) | Formulation ratio (%) | Amount loaded (g) | Formulation ratio (%) | Amount loaded (g) | Formulation ratio (%) | Amount loaded (g) | Formulation ratio (%) |
| Drug-containing hollow particles | Compound A (ground product of JM) | 2.504 | 38.4 | 360 | 64.1 | 288.3 | 64.1 | 560 | 64.0 |
| | Aminoalkyl methacrylate copolymer RS (No. 100 on) | 0.626 | 9.6 | 90 | 16.0 | 72.1 | 16.0 | 140 | 16.0 |
| | Talc (NANO ACE ® D-1000) | — | — | 112 | 19.9 | — | — | — | — |
| | Talc (Micro Ace ® P-3) | — | — | — | — | — | — | — | — |
| | Talc (high-grade talc MSP) | — | — | — | — | 89.6 | 19.9 | — | — |
| | Talc (sodium bicarbonate talc H) | — | — | — | — | — | — | 175 | 20.0 |
| Outer layer tablet component | D-mannitol (PEARLITOL 200 SD) | 2.34 | 36.0 | — | — | — | — | — | — |
| | Crystalline cellulose (Ceolus PH-101 | 0.98 | 15.0 | — | — | — | — | — | — |
| | | 0.98 | 15.0 | — | — | — | — | — | — |
| | Magnesium stearate | 0.07 | 1.0 | — | — | — | — | — | — |
| Total | | 6.52 | 100 | 562 | 100 | 450 | 100 | 875 | 100 |

Example 5

Coated Component of Interest-Containing Hollow Particles Using Particles with Differences in Each of Particle Size, Water Solubility, Wettability, and Swellability Coated component of interest-containing hollow particles using particles with different particle size, water solubility, wettability, and swellability were manufactured in Example 5.

TABLE 7

| Name of substance | Name of product | Manufacturer | Organic/ Inorganic | Water solubility | Shape | Swelling | Particle size (median size) |
|---|---|---|---|---|---|---|---|
| Hydrogenated oil | Lubriwax-101 | Freund Corporation | Organic | Insoluble | Indeterminate shape | x | 22 um |
| Magnesium stearate | Vegetable magnesium stearate | Taihei Chemical | Organic salt | Insoluble | Indeterminate shape | x | 7 um |
| Sodium stearyl fumarate | PRUV ® | JRS Pharma | Organic | Insoluble | Indeterminate shape | x | 22 um |
| Talc | Micro Ace P-3 | Nippon Talc | Inorganic | Insoluble | Disc shape | x | 5 um |
| Titanium oxide | Titanium oxide NA61 | Toho Titanium | Inorganic | Insoluble | Spherical | x | 1 um |
| Crystalline cellulose | PH-F20JP | Asahi Kasei Chemicals | Organic | Insoluble | Fibrous | o | 20 um |
| Alginic acid | Alginic acid G (ground JM) | Kimica | Organic | Soluble | Indeterminate shape | x | 20 um |

TABLE 8

Formulation of Examples 5-1 to 5-5 and Example 6

| | Example 5-1 | | Example 5-2 | | Example 5-3 | | Example 5-4 | | Example 5-5 | | Example 6 | |
|---|---|---|---|---|---|---|---|---|---|---|---|---|
| | Amount Loaded (%) | Formulation (%) | Amount Loaded (%) | Formulation (%) | Amount Loaded (%) | Formulation (%) | Amount Loaded (%) | Formulation (%) | Amount Loaded (%) | Formulation (%) | Amount Loaded (%) | Formulation (%) |
| Compound A (ground product of JM) | 560 | 64 | 350 | 62 | 560 | 64 | 288.3 | 64 | 324 | 64 | 400 | 72 |
| Aminoalkyl methacrylate copolymer RS No. 100 cm | 140 | 16 | 100 | 18 | 140 | 16 | 72.1 | 16 | 81 | 16 | 100 | 18 |
| Hydrogenated oil | 175 | 20 | — | — | — | — | — | — | — | — | — | — |
| Magnesium stearate | — | — | 113 | 20 | — | — | — | — | — | — | — | — |
| Sodium stearyl fumarate | — | — | — | — | 178 | 20 | — | — | — | — | — | — |
| Titanium oxide | — | — | — | — | — | — | 89.6 | 20 | — | — | — | — |
| Crystalline cellulose (Ceolus PH-F20JP) | — | — | — | — | — | — | — | — | 102 | 20 | — | — |
| Alginic acid | — | — | — | — | — | — | — | — | — | — | 55 | 9.9 |
| (Aqueous 95% ethanol solution) manufacture of nuclear particles) | (175) | (20) | (125) | (25) | (115) | (13) | (96) | (19) | (100) | (20) | (93) | (17.2) |
| (Aqueous 95% ethanol solution for coating) | (185) | (21) | (45) | (8) | (20) | (2) | (75) | (17) | (165) | (33) | (85) | (15.3) |
| Total | 875 | 100 | 563 | 100 | 875 | 100 | 450 | 100 | 507 | 100 | 555 | 100 |

Test Example 4

Dissolution Test on Coated Component of Interest-Containing Hollow Particles Using Particles with Differences in Each of Particle Size, Water Solubility, Wettability, and Swellability A dissolution test was conducted using the coated component of interest-containing hollow particles manufactured in Example 5. The list of tested formulations is shown in Table 8. The test conditions were the same as Test Example 1. The results are shown in FIG. 5. Table 13 shows the ratio of 50% dissolution times before and after coating. The dissolution time was extended by a factor of 2 or greater. Improvement in the ability to control release of macromolecules constituting nuclear particles was confirmed for all coated component of interest-containing hollow particles using water insoluble particles as coatable microparticles.

Example 6

Particles Coated with Water Soluble Particles

Particles coated with water soluble particles were manufactured in Example 6. Table 7 shows the particle size, water solubility, shape, and swellability of water soluble particles (alginic acid) that were used.

Example 6 was manufactured by the same method as Example 1 in accordance with the formulation ratio and amount loaded described in Table 8. Specifically, compound A and granularity controlled product of aminoalkyl methacrylate copolymer RS (No. 100 ON fraction) were loaded into a high speed stirring granulator (model FM-VG-05, capacity: 5 L, Powrex Corp) and granulated while spraying a predetermined amount of aqueous 95% ethanol solution under the mixing and granulating conditions shown in Table 2-1 to obtain nuclear particles in a wet powder state. Subsequent to the above step, coatable microparticles, i.e., alginic acid, were loaded into a high speed stirring granulator containing the nuclear particles in accordance with Table 8. Coating granulation was performed while spraying a predetermined amount of aqueous 95% ethanol solution under the coating granulation conditions shown in Table 2-1. The resulting particles were then subjected to fluidized bed drying using Multiplex model MP-01 (Powrex Corp) to obtain the coated component of interest-containing hollow particles of Example 6. Table 13 shows the coating time and time that was required for manufacture of the resulting particles.

Example 7

Manufacture of Coated Component of Interest-Containing Hollow Particles Using Nuclear Particles for Coating with Different Constituent Macromolecules Coated component of interest-containing hollow particles using nuclear particles for coating with different constituent macromolecules were manufactured in Example 7.

Examples 7-1 and 7-2 were manufactured by the same method as Example 1 in accordance with the formulation ratio and amount loaded described in Table 9. Specifically, compound A and granularity controlled product of aminoalkyl methacrylate copolymer E100 (No. 60-100 fraction) or granularity controlled product of dried methacrylate copolymer L 100-55 (No. 150-200 fraction) were loaded into a high speed stirring granulator (model FM-VG-05, capacity: 5 L, Powrex Corp) and granulated while spraying a predetermined amount of aqueous 95% ethanol solution under the mixing and granulating conditions shown in Table 2-1 to obtain nuclear particles in a wet powder state. Subsequent to the above step, coatable microparticles, i.e., talc (Micro Ace P-3), were loaded into a high speed stirring granulator containing the nuclear particles in accordance with Table 9. Coating granulation was performed while spraying a predetermined amount of aqueous 95% ethanol solution under the coating granulation conditions shown in Table 2-1. The resulting particles were then subjected to fluidized bed drying using Multiplex model MP-01 (Powrex Corp) to obtain the coated component of interest-containing hollow particles of Examples 7-1 and 7-2. Table 13 shows the coating time and time that was required for manufacture of the resulting particles.

TABLE 9

| | Example 7-1 | | Example 7-2 | | Comparative Example 7-1 | | Comparative Example 7-2 | |
| --- | --- | --- | --- | --- | --- | --- | --- | --- |
| | Amount loaded (g) | Formulation ratio (%) | Amount loaded (g) | Formulation ratio (%) | Amount loaded (g) | Formulation ratio (%) | Amount loaded (g) | Formulation ratio (%) |
| Compound A (ground product of JM) | 420 | 60 | 388.9 | 62 | 560 | 80 | 560 | 80 |
| Aminoalkyl methacrylate copolymer E (No. 60-100) | 140 | 20 | — | — | 140 | 20 | — | — |
| Methacrylate L copolymer L 100-55 (No. 150-200) | — | — | 111.1 | 10 | — | — | 140 | 20 |
| Talc (Micro Ace ® P-3) | 140 | 20 | 125 | 20 | — | — | — | — |
| (Aqueous 95% ethanol solution) (for nuclear particles) | (110) | (16) | (96) | (15) | (260) | (37) | (215) | (31) |
| Aqueous 95% ethanol solution (for coating) | (20) | (3) | (185) | (30) | — | — | — | — |
| Total | 700 | 100 | 625 | 100 | 700 | 100 | 700 | 100 |

Comparative Example 7

Manufacture of Nuclear Particles for Coating with Different Macromolecules Constituting Nuclear Particles Comparative Example 7 manufactured component of interest-containing hollow particles that are nuclear particles using nuclear particles for coating comprised of stomach soluble or enteric macromolecules.

Comparative Examples 7-1 and 7-2 were manufactured by the same method as Example 1 in accordance with the formulation ratio and amount loaded described in Table 9. Specifically, compound A and granularity controlled product of aminoalkyl methacrylate copolymer E 100 (No. 60-100 fraction) or granularity controlled product of dried methacrylate copolymer L 100-55 (No. 150-200 fraction) were loaded into a high speed stirring granulator (model FM-VG-05, capacity: 5 L, Powrex Corp) and granulated while spraying a predetermined amount of aqueous 95% ethanol solution under the mixing and granulating conditions shown in Table 2-1 to obtain nuclear particles in a wet powder state. The resulting particles were then subjected to fluidized bed drying using Multiplex model MP-01 (Powrex Corp) to obtain the component of interest-containing hollow particles that are nuclear particles of Examples 7-1 and 7-2.

Example 8

Manufacture of Tablets Comprising Coated Component of Interest-Containing Hollow Particles Using Nuclear Particles for Coating with Different Constituent Macromolecules Tablets of Example 8-1 were manufactured by weighing an additive, mixing, and tableting in accordance with the formulation ratio and amount loaded in Table 10 using the coated particles obtained in Example 7-1.

Specifically, the ingredients were weighed in accordance with Table 10 and manually mixed using a plastic bag. The resulting mixed powder was tableted with a tabletop press TB-20H (NPA System) (flat tablet Φ8 mm, tableting pressure: 6 kN). The prepared tablets were subjected to a dissolution test in accordance with Test Example 1.

TABLE 10

|  |  | Example 8-1 | | Comparative Example 8-1 | | Comparative Example 8-2 | |
| --- | --- | --- | --- | --- | --- | --- | --- |
|  |  | Amount loaded (g) | Formulation ratio (%) | Amount loaded (g) | Formulation ratio (%) | Amount loaded (g) | Formulation ratio (%) |
| Drug-containing hollow particles | Compound A (ground product of JM) | 50.04 | 38.5 | 50 | 38.5 | 50 | 38.5 |
|  | Methacrylate copolymer E (no. 60-100) | 16.68 | 12.8 | 12.5 | 9.6 | — | — |
|  | Methacrylate copolymer L 100-55 (no. 150-200) | — | — | — | — | 12.5 | 9.6 |
|  | Talc (Micro Ace P-3) | 16.68 | 12.8 | — | — | — | — |
| Outer layer tablet component | D-mannitol (PEARLITOL 200 SD) | 33.0 | 25.4 | 53.2 | 40.9 | 53.2 | 40.9 |
|  | Crystalline cellulose (Ceolus PH-101) | 13.0 | 10.0 | 13.0 | 10.0 | 13.0 | 10.0 |
|  | Magnesium stearate | 0.7 | 0.5 | 1.3 | 1.0 | 1.3 | 1.0 |
| Total |  | 130.1 | 100 | 130 | 100 | 130 | 100 |

Comparative Example 8

Manufacture of Tablets Comprising Nuclear Particles for Coating with Different Macromolecules Constituting Nuclear Particles Comparative Examples 8-1 and 8-2, which are tablets comprising nuclear particles for coating manufactured in Comparative Example 7, were manufactured by weighing an additive, mixing, and tableting in accordance with the formulation ratio and amount loaded in Table 10, as in Example 8.

Test Example 5

Dissolution Test on Tablets and Component of Interest-Containing Hollow Particles Using Nuclear Particles for Coating with Different Constituent Macromolecules A dissolution test was conducted using the particles manufactured in Example 7-2 and tablets manufactured in Example 8-1 and Comparative Examples 8-1 and 8-2. The test conditions were the same as in Test Example 1. The results are shown in FIGS. 6 to 9.

Regardless of the type of macromolecule, the function of macromolecules constituting nuclear particles was able to be improved by the coating of the present application.

Example 9

Manufacture of Nifedipine Photostabilized Particles

In accordance with the formulation ratio and amount loaded in Table 11, compound B and 140 g of granularity controlled product of hydroxypropyl cellulose (HPC-L) (No. 60-100) were loaded into a high speed stirring granulator (model FM-VG-05, capacity: 5 L, Powrex Corp) and granulated while spraying 165 g of aqueous 95% ethanol solution under the mixing and granulating conditions shown in Table 2-1 to obtain nuclear particles in a wet powder state. Subsequent to the above step, 78 g of coatable microparticles, i.e., titanium oxide (NA61), were loaded into a high speed stirring granulator containing the nuclear particles. Coating granulation was performed while spraying 28 g of aqueous 95% ethanol solution under the coating granulation conditions shown in Table 2-1. The resulting particles were then subjected to fluidized bed drying using Multiplex model MP-01 (Powrex Corp). The nuclear particles for coating were manufactured twice. 800 g thereof, 179.2 g of titanium oxide, and 11 g of Red Ferric Oxide were loaded into a stirring granulator. Granulation was performed while spraying 130 g of aqueous 95% ethanol solution under the mixing and granulation conditions shown in Table 2-1 to obtain nuclear particles in a wet powder state. The resulting particles were then subjected to fluidized bed drying using Multiplex model MP-01 (Powrex Corp) to obtain 910 g of coated component of interest-containing hollow particles. Table 13 shows the coating rate, coating time, and time that was required for manufacture of the resulting particles.

TABLE 11

|  | Example 9 | | Comparative Example 9 |
|---|---|---|---|
|  | Formulation ratio (%) | Amount loaded (g) | Formulation ratio (%) |
| Compound B (ground TM) | 63.3 | 560 | 80.0 |
| HPC-L (No. 60-100) | 15.8 | 140 | 20.0 |
| Titanium oxide | 19.7 | — | — |
| Red Ferric Oxide | 1.2 | — | — |
| Aqueous 95% ethanol solution | 16.3 | 178 | 25.4 |
| total | 100 | 700 | 100 |

Comparative Example 9

Manufacture of Nifedipine Particles

Nifedipine particles were manufactured by the same method as Example 9. Compound B and 140 g of granularity controlled product of hydroxypropyl cellulose (HPC-L) (no. 60-100) were loaded into a high speed stirring granulator (model FM-VG-05, capacity: 5 L, Powrex Corp) and granulated while spraying 178 g of aqueous 95% ethanol solution under the mixing and granulating conditions shown in Table 2-1 to obtain nuclear particles in a wet powder state. Subsequently, the resulting particles were subjected to fluidized bed drying using Multiplex model MP-01 (Powrex Corp) to obtain Comparative Example 9.

Test Example 6

Photostability Test

The particles manufactured in Example 9 and Comparative Example 9 were placed in photostability testing chamber (model LT-120, Nagano Science Co. Ltd.) and irradiated with 600000 Lux·hr or 1200000 Lux·hr as the total illuminance at 3000 Lux/hr. The content of particles after irradiation was measured in line with the nifedipine quantification method in the Revised 16th Japanese Pharmacopoeia. Specifically, 0.12 mg equivalent of particles was accurately measured and dissolved into methanol to accurately prepare a 200 mL solution. 5 mL of the solution was accurately measured. Methanol was added thereto to accurately prepare 100 mL of solution. The solution was tested by ultraviolet visible spectrophotometry to measure absorbance A at a wavelength absorbing a wavelength of 350 nm. The amount of nifedipine was calculated from the measured absorbance and the following equation. The test results are shown in FIG. 10. Improved photostability has been confirmed in Example 9 which was coated with light blocking components titanium oxide and Red Ferric Oxide.

Amount of nifedipine (mg)=$A$/142.3×40000

Example 10

Particles Containing Multiple Active Pharmaceutical Ingredients

In accordance with the formulation ratio and amount loaded in Table 12, compound A and aminoalkyl methacrylate copolymer RS (No. 100-140) were loaded into a high speed stirring granulator (model FM-VG-05, capacity: 5 L, Powrex Corp) and granulated while spraying 165 g of aqueous 95% ethanol solution under the mixing and granulating conditions shown in Table 2-1 to obtain nuclear particles in a wet powder state. Subsequent to the above step, 51 g of coatable microparticles, i.e., compound C, were loaded into a high speed stirring granulator containing the nuclear particles. Coating granulation was performed while spraying 11 g of aqueous 95% ethanol solution under the coating granulation conditions shown in Table 2-1. The resulting particles were then subjected to fluidized bed drying using Multiplex model MP-01 (Powrex Corp) to obtain coated component of interest-containing hollow particles. FIG. 11 shows the appearance and cross-section. Table 13 shows the coating time and time that was required for manufacture of the resulting particles.

TABLE 12

|  | Example 10 | |
|---|---|---|
|  | Amount loaded (g) | Formulation ratio (%) |
| Compound A | 509 | 58.1 |
| Compound C | 51 | 5.8 |
| Aminoalkyl methacrylate copolymer 140 RS (No. 100-140) | 140 | 16.0 |
| Aqueous 95% ethanol solution (manufacture of nuclear particles) | 165 | 18.9 |
| Aqueous 95% ethanol solution (coating) | 11 | 1.3 |
| total | 876 | 100 |

TABLE 13

| | | Comparative Example 1 | Example 1-1 | Example 1-2 | Example 1-3 | Example 2 | Example 2-1 | Example 2-2 |
|---|---|---|---|---|---|---|---|---|
| Calculation of coating rate of manufactured formulation | Measurement value of content (%) | — | — | — | — | — | — | — |
| | Coating ratio (%) | — | — | — | — | — | — | — |
| Calculation of manufacturing time | Amount of solvent used (g)* | — | 7 | 28 | 30 | — | — | — |
| | Coating time (minutes) | — | 0.875 | 3.5 | 3.75 | — | — | — |
| | Drying time (minutes) | — | 10 | 10 | 10 | — | — | — |
| | Manufacturing time (minutes) | — | 10.875 | 13.5 | 13.75 | — | — | — |
| 50% dissolution time | 50% dissolution time (JP 1st) (minutes) | 106.33 | — | — | — | 49.86 | 201.11 | 352.91 |
| Ratio of 50% dissolution time with respect to nucleus | Ratio of 50% dissolution time with respect to nucleus (JP 1st) | — | — | — | — | — | 4.03 | 7.08 |

*After granulation, some transitioned into coating step without drying, and some were coated after drying

| | | Example 2-3 | Example 4-1 | Example 4-2 | Example 4-3 | Example 5-1 | Example 5-2 | Example 5-3 |
|---|---|---|---|---|---|---|---|---|
| Calculation of coating rate of manufactured formulation | Measurement value of content (%) | — | — | 104.3 | — | — | — | — |
| | Coating ratio (%) | — | — | 87.1 | — | — | — | — |
| Calculation of manufacturing time | Amount of solvent used (g)* | — | 190 | 100 | 48 | 185 | 45 | 20 |
| | Coating time (minutes) | — | 23.75 | 12.5 | 6 | 23.125 | 5.625 | 2.5 |
| | Drying time (minutes) | — | 10 | 10 | 10 | 10 | 11 | 12 |
| | Manufacturing time (minutes) | — | 33.75 | 22.5 | 16 | 33.125 | 16.625 | 14.5 |
| 50% dissolution time | 50% dissolution time (JP 1st) (minutes) | 1784.79 | 2061.00 | 4144.19 | 3900.00 | 1387.32 | 348.90 | 29760.00 |
| Ratio of 50% dissolution time with respect to nucleus | Ratio of 50% dissolution time with respect to nucleus (JP 1st) | 35.79 | 19.38 | 38.97 | 36.68 | 13.05 | 3.28 | 279.88 |

*After granulation, some transitioned into coating step without drying, and some were coated after drying

| | | Example 5-4 | Example 5-5 | Example 6 | Example 7-1 | Example 7-2 | Example 9 | Example 10 |
|---|---|---|---|---|---|---|---|---|
| Calculation of coating rate of manufactured formulation | Measurement value of content (%) | 100.4 | — | — | — | — | 100 | — |
| | Coating ratio (%) | 93.9 | — | — | — | — | 100 | — |
| Calculation of manufacturing time | Amount of solvent used (g)* | 75 | 165 | 85 | 20 | 185 | 130 | 11 |
| | Coating time (minutes) | 9.375 | 20.625 | 10.625 | 2.5 | 23.125 | 18.25 | 1.375 |
| | Drying time (minutes) | 13 | 10 | 14 | 15 | 16 | 16 | 16 |
| | Manufacturing time (minutes) | 22.375 | 30.625 | 24.625 | 17.5 | 39.125 | 32.25 | 17.375 |
| 50% dissolution time | 50% dissolution time (JP 1st) (minutes) | 652.02 | 220.05 | — | — | — | — | — |

TABLE 13-continued

| | | | | | | | |
|---|---|---|---|---|---|---|---|
| Ratio of 50% dissolution time with respect to nucleus | Ratio of 50% dissolution time with respect to nucleus (JP 1st) | 6.13 | 2.07 | — | — | — | — |

*After granulation, some transitioned into coating step without drying, and some were coated after drying

| | | Example 11-1 | Example 11-2 | Example 11-3 | Comparative Example 12B |
|---|---|---|---|---|---|
| Calculation of coating rate of manufactured formulation | Measurement value of content (%) | 99.7 | 100.7 | 95.3 | — |
| | Coating ratio (%) | 100.5 | 98.8 | 92.6 | — |
| Calculation of manufacturing time | Amount of solvent used (g)* | 118 | 150 | 80 | 225 |
| | Coating time (minutes) | 14.75 | 18.75 | 10 | 27 |
| | Drying time (minutes) | 14 | 14 | 14 | 5 |
| | Manufacturing time (minutes) | 28.75 | 32.75 | 24 | 32 |
| 50% dissolution time | 50% dissolution time (JP 1st) (minutes) | 783.35 | 106.38 | 3382.76 | 58.58 |
| Ratio of 50% dissolution time with respect to nucleus | Ratio of 50% dissolution time with respect to nucleus (JP 1st) | 63.98 | 21.15 | 235.86 | 0.55 |

*After granulation, transitioned into coating step without drying

It is understood that coating in the present invention is efficient, requires a short period of time, and has a sustained releasing property.

The particle size of coatable microparticles is described in Table 14.

TABLE 14

| | Measurement data | | | | Mesh size at which all particles pass | |
|---|---|---|---|---|---|---|
| | D50 | D90 | D99 | D100 | Mesh | μm |
| Talc (Micro Ace P-3) | 3.49 | 8.32 | 14.47 | 25 | 500 | 25 |
| Talc (NANO ACE D-1000) | 1.81 | 4.78 | 8.8 | 12.5 | 635 | 20 |
| Talc (High grade talc MSP) | 8.09 | 27.26 | 49.06 | 87 | 170 | 90 |
| Talc (sodium bicarbonate talc H) | — | — | — | — | — | — |
| Lubriwax-101 | 25.28 | 64.48 | 103.26 | 147 | 100 | 150 |
| Vegetable magnesium stearate | 3.51 | 19.52 | 47.78 | 87 | 170 | 90 |
| Sodium stearyl fumarate | 9.63 | 22.81 | 38.1 | 73 | 200 | 75 |
| Titanium oxide | 6.92 | 19.79 | 52.29 | 73 | 200 | 75 |
| Alginic acid | — | — | — | — | — | — |
| Crystalline cellulose (Ceolus PH-F20JP) | 16.66 | 40.3 | 69.11 | 87 | 170 | 90 |

Example 11

Nuclear particles for coating were manufactured in accordance with Table 15. Specifically, aminoalkyl methacrylate copolymer RS (Eudragit RSPO) and compound E, F, or G were loaded as powder into a high speed stirring granulator, Vertical Granulator (model FM-VG-05, capacity: 5 L, Powrex Corp) at the amounts described in Table 15 and then granulated while spraying a predetermined amount of aqueous 95% ethanol solution under the mixing and granulating conditions shown in Table 2-1 to obtain nuclear particles in a wet powder state. Subsequent to the above step, a coating additive, i.e., talc (Micro Ace® P-3), was loaded as powder, at 40% by weight with respect to the amount loaded, into a high speed stirring granulator containing the nuclear particles. Coating granulation was performed while spraying a predetermined amount of aqueous 95% ethanol solution under the coating granulation conditions shown in Table 2-1. The coated component of interest-containing hollow particles in a wet powder state were then subjected to fluidized bed drying using Multiplex model MP-01 (Powrex Corp) to obtain the coated component of interest-containing hollow particles of Examples 11-1, 11-2, and 11-3.

Comparative Example 11

In Comparative Examples 11-1, 11-2, and 11-3, only particles that were not coated, i.e., nuclear particles for coating, were manufactured in accordance with the formulation ratio and amount loaded described in Table 15 in the same manner as Example 11. After granulating nuclear particles for coating in a wet powder state as in Example 1, the nuclear particles for coating in a wet powder state were subjected to rack drying using a Multiplex model MP-01 (Powrex Corp) to obtain the nuclear particles for coating of Comparative Examples 11-1, 11-2, and 11-3.

nuclear particles. Coating granulation was performed while spraying a predetermined amount of aqueous 95% ethanol solution under the coating granulation conditions shown in

TABLE 15

|  | Comparative Example 11-1 | | Comparative Example 11-2 | | Comparative Example 11-3 | | Example 11-1 | | Example 11-2 | | Example 11-3 | |
| --- | --- | --- | --- | --- | --- | --- | --- | --- | --- | --- | --- | --- |
|  | Amount loaded (g) | Formulation ratio (%) | Amount loaded (g) | Formulation ratio (%) | Amount loaded (g) | Formulation ratio (%) | Amount loaded (g) | Formulation ratio (%) | Amount loaded (g) | Formulation ratio (%) | Amount loaded (g) | Formulation ratio (%) |
| Compound E | 560 | 80 | — | — | — | — | 560 [480] | 48.0 | — | — | — | — |
| Compound F | — | — | 560 | 80 | — | — | — | — | 580 [480] | 48.0 | — | — |
| Compound G | — | — | — | — | 560 | 80 | — | — | — | — | 560 [480] | 48.0 |
| Aminoalkyl methacrylate copolymer RS (No. 100 cm) | 140 | 20 | 140 | 20 | 140 | 20 | 140 [120] | 12.0 | 140 [120] | 12.0 | 140 [120] | 12.0 |
| Talc (Micro Ace P-3) | — | — | — | — | — | — | 467 [400] | 40.0 | 467 [400] | 40.0 | 467 [400] | 40.0 |
| (Aqueous 95% ethanol solution) nuclear particles | (125) | — | (187) | — | (164) | — | — | — | — | — | — | — |
| (Aqueous 95% ethanol solution) (coating) | — | — | — | — | — | — | (118) | — | (150) | — | (80) | — |
| Total | 700 | 700 | 700 | 700 | 700 | 100 | 1167 | 100 | 1167 | 100 | 1167 | 100 |

The numerical values in the parentheses under amount loaded for compounds E, F, and G in Examples 11-1, 11-2, and 11-3 indicate the amount when the total amount is 1000 g.

Example 11A

Nuclear particles for coating are manufactured in accordance with Table 15A. Specifically, aminoalkyl methacrylate copolymer RS (Eudragit RSPO) and compound A were loaded into a high speed stirring granulator, Vertical Granulator (model FM-VG-05, capacity: 5 L, Powrex Corp), as powder at the amount described in Table 15A and then granulated while spraying a predetermined amount of aqueous 95% ethanol solution under the mixing and granulating conditions shown in Table 2-1 to obtain nuclear particles for coating in a wet powder state. Subsequent to the above step, a coating additive, i.e., talc (Micro Ace® P-3), was loaded as powder, at 40% by weight with respect to the amount loaded, into a high speed stirring granulator containing the nuclear particles. Coating granulation was performed while spraying a predetermined amount of aqueous 95% ethanol solution under the coating granulation conditions shown in Table 2-1. The coated component of interest-containing hollow particles in a wet powder state were then subjected to fluidized bed drying using Multiplex model MP-01 (Powrex Corp) to obtain the coated component of interest-containing hollow particles of Examples 11A-1 and 11A-2.

Comparative Example 11A

In Comparative Examples 11A-1, 11A-2, and 11A-3, only particles that were not coated, i.e., nuclear particles for coating, were manufactured in accordance with the formulation ratio and amount loaded described in Table 15A in the same manner as Example 11A. After granulating nuclear particles for coating in a wet powder state as in Example 1, the nuclear particles for coating in a wet powder state were subjected to rack drying using a Multiplex model MP-01 (Powrex Corp) to obtain the nuclear particles for coating of Comparative Examples 11A-1, 11A-2, and 11A-3.

TABLE 15A

|  | Example 11A-1 | | Example 11A-2 | | Comparative Example 11A-1 | | Comparative Example 11A-2 | |
| --- | --- | --- | --- | --- | --- | --- | --- | --- |
|  | Amount loaded (g) | Formulation ratio (%) | Amount loaded (g) | Formulation ratio (%) | Amount loaded (g) | Formulation ratio (%) | Amount loaded (g) | Formulation ratio (%) |
| Acetaminophen (JM) | 480 | 60 | — | — | 560 | 80 | — | — |
| Anhydrous caffeine | — | — | 480 | 60 | — | — | 560 | 80 |
| Eudragit RSPO (No. 100-140) | 120 | 20 | 120 | 20 | 140 | 20 | 140 | 20 |
| Talc (Micro Ace P-3) 95% ethanol Nuclear particles 95% ethanol Coating | 400 | 40 | 400 | 20 | — | — | — | — |
| total | 1000 | 100 | 1000 | 100 | 700 | 100 | 700 | 100 |

Comparative Example 12A

Nuclear particles for coating were manufactured according to Table 16A. Specifically, aminoalkyl methacrylate copolymer RS (Eudragit RSPO) and compound A were loaded into a high speed stirring granulator, Vertical Granulator (model FM-VG-05, capacity: 5 L, Powrex Corp), as powder at the amount described in Table 16A and then granulated while spraying a predetermined amount of aqueous 95% ethanol solution under the mixing and granulating conditions shown in Table 2-1. Component of interest-containing hollow particles that are nuclear particles in a wet powder state were subjected to fluidized bed drying using Multiplex model MP-01 (Powrex Corp) to obtain nuclear particles for coating. A coating additive, i.e., talc (Micro Ace® P-3), was loaded as powder, at 20% by weight with respect to the amount loaded, into Multiplex model MP-01 containing the nuclear particles. Coating granulation was performed while spraying a predetermined amount of aqueous 95% ethanol solution. The coated component of interest-containing hollow particles in a wet powder state were then subjected to fluidized bed drying using Multiplex model MP-01 (Powrex Corp) to obtain the component of interest-containing hollow particles of Example 12A.

TABLE 16A

| | Comparative Example 12A | |
|---|---|---|
| | Amount loaded (g) | Formulation ratio (%) |
| Zonisamide | 420 | 60 |
| Eudragit RSPO (No. 100-140) | 140 | 20 |
| Talc (Micro Ace P-3) | 140 | 20 |
| 95% ethanol Nuclear particles | | |
| 95% ethanol Coating | | |
| total | 700 | 100 |

Comparative Example 12B

Nuclear particles for coating were manufactured according to Table 16B. Specifically, aminoalkyl methacrylate copolymer RS (Eudragit RSPO) and compound A were loaded into a high speed stirring granulator, Vertical Granulator (model FM-VG-05, capacity: 5 L, Powrex Corp), as powder at the amount described in Table 16B and then granulated while spraying a predetermined amount of aqueous 95% ethanol solution under the mixing and granulating conditions shown in Table 2-1. Component of interest-containing hollow particles that are nuclear particles in a wet powder state were subjected to fluidized bed drying using Multiplex model MP-01 (Powrex Corp) to obtain nuclear particles for coating. A coating additive, i.e., sodium stearyl fumarate, was loaded as powder, at 20% by weight with respect to the amount loaded, into Multiplex model MP-01 containing the nuclear particles. Coating granulation was performed while spraying a predetermined amount of aqueous 95% ethanol solution. The coated component of interest-containing hollow particles in a wet powder state were then subjected to fluidized bed drying using Multiplex model MP-01 (Powrex Corp) to obtain the coated component of interest-containing hollow particles of Example 12B.

TABLE 16B

| | Comparative Example 12B | |
|---|---|---|
| | Amount loaded (g) | Formulation ratio (%) |
| Compound A | 538.16 | 64.1 |
| Eudragit RSPO (No. 100-on) | 134.59 | 16 |
| Sodium stearyl fumarate | 167.25 | 19.9 |
| (95% aqueous ethanol solution) (Nuclear particles) | (235) | — |
| (95% aqueous ethanol solution) (Coating) | (225) | — |
| total | 840 | 100 |

Comparative Example 13-1

<Component of Interest-Containing Nuclear Particles>

The raw materials described in Table 18 were loaded into a stirring granulator (FM-VG-05, Powrex Corp) for 2 minutes of preliminary mixing (stirring blade speed of 400 $min^{-1}$; crushing blade speed of 3000 $min^{-1}$, all mixing operations were performed under the same stirring conditions). Granulation was performed by mixing while spraying anhydrous ethanol to obtain component of interest-containing nuclear particles in a wet powder state. The wet powder particles were loaded into and dried with a fluidized bed granulator (MP-01, Powrex Corp) to obtain the component of interest-containing nuclear particles. Magnesium aluminometasilicate was further added to the fluidized bed granulator and mixed to obtain Comparative Example 13-1.

Example 13-1

After manufacturing component of interest-containing nuclear particles in a wet powder state in the same manner as Comparative Example 13-1, the particles were dried and mixed for 1 minute. Subsequently, a half an amount of sodium stearyl fumarate was loaded into a stirring granulation as powder, and the component of interest-containing nuclear particles were mixed while spraying anhydrous ethanol for coating. After drying and mixing for 1 minute in the same manner as above, ¼ amount of sodium stearyl fumarate was added, and the particles were mixed while spraying with anhydrous ethanol for coating. Furthermore, a mixture of ¼ amount of sodium stearyl fumarate and Yellow Ferric Oxide was added and mixed while spraying anhydrous ethanol for coating. The coating granules were dried with a fluidized bed dryer. Magnesium aluminometasilicate was further added and mixed in the fluidized bed dryer to obtain Example 13-1. The amount of each raw material loaded of Example 13-1 is described in Table 19.

Example 13-2 and Comparative Example 13-2

Each component was weighed in accordance with Table 20 and mixed in a V blender. The mixed tablet powder was tableted with a rotary tablet press (mallet: 8 mmφ, 12R) to obtain Example 13-2 and Comparative Example 13-2.

Test Example 7

Sensory evaluation on Example 13-2 and Comparative Example 13-2 was conducted (FIG. 12). This test strictly abided by the rules for confirming that the formulation does not have bioabsorbability in the mouth and spitting the formulation out after the test in view of safety. 5 subjects participated. Each sample was put into the mouth and kept in the mouth until the formulation disintegrated, and then spat out. Bitterness was evaluated while holding the formulation in the mouth, when spat out (immediately after disintegration), and 1 minute after spitting out. Two levels of bitterness, i.e., acceptable and unacceptable, were used. If the mean score was 0.5 or less, it was determined that the degree of bitterness was not problematic for dosing. If the mean score was 1.0 or greater, it was determined that dosing is difficult due to bitterness.

Score "0": no bitterness
Score "0.5": sensation of slight bitterness
Score "1.0": bitter
Score "1.5": strong but tolerable bitterness
Score "2.0": strong and intolerable bitterness As a result of the bitterness evaluation test, Example 13-2 had an acceptable taste, but Comparative Example 13-2 had a strongly bitter and unacceptable taste.

In view of Test Example 7, Example 13-2 was found to have a better bitterness masking effect over Comparative Example 13-2. It is now clear that Example 13-2 is a desirable formulation with a feature of "high bitterness masking property".

TABLE 18

|  | Comparative Example 13-1 Amount loaded (g) |
| --- | --- |
| Compound D | 240.00 |
| Aminoalkyl methacrylate copolymer RS | 144.00 |
| Aspartame | 120.00 |
| D-mannitol (PEARLITOL 25C) | 264.00 |
| Anhydrous ethanol | q.s. |
| Magnesium aluminometasilicate | 4.80 |
| Total | 772.80 |

TABLE 19

|  | Example 13-1 Amount loaded (g) |
| --- | --- |
| Compound D | 240.00 |
| Aminoalkyl methacrylate copolymer RS | 144.00 |
| Aspartame | 120.00 |
| D-mannitol | 264.00 |
| Anhydrous ethanol | q.s. |
| Sodium stearyl fumarate | 191.52 |
| Yellow Ferric Oxide | 0.48 |
| Magnesium aluminometasilicate | 4.80 |
| Total | 964.80 |

TABLE 20

|  | Example 13-2 Amount loaded (g) | Comparative Example 13-2 Amount loaded (g) |
| --- | --- | --- |
| Example 13-1 | 80.40 | — |
| Comparative Example 13-1 | — | 64.40 |
| PEARLITOL FLASH | 43.60 | 43.60 |
| Crystalline cellulose (CeolusKG-1000) | 10.00 | 10.00 |
| Crystalline cellulose (CeolusUF-702) | 40.00 | 40.00 |
| Corn starch | 19.80 | 19.80 |
| Yellow Ferric Oxide | 0.20 | 0.20 |
| Aspartame | 4.00 | 4.00 |
| Flavoring agent | 0.20 | 0.20 |
| Magnesium aluminometasilicate | 1.00 | 1.00 |
| Sodium stearyl fumarate | 1.00 | 1.00 |
| Total | 200.2 | 184.2 |

Test Example 8

Figure 14:
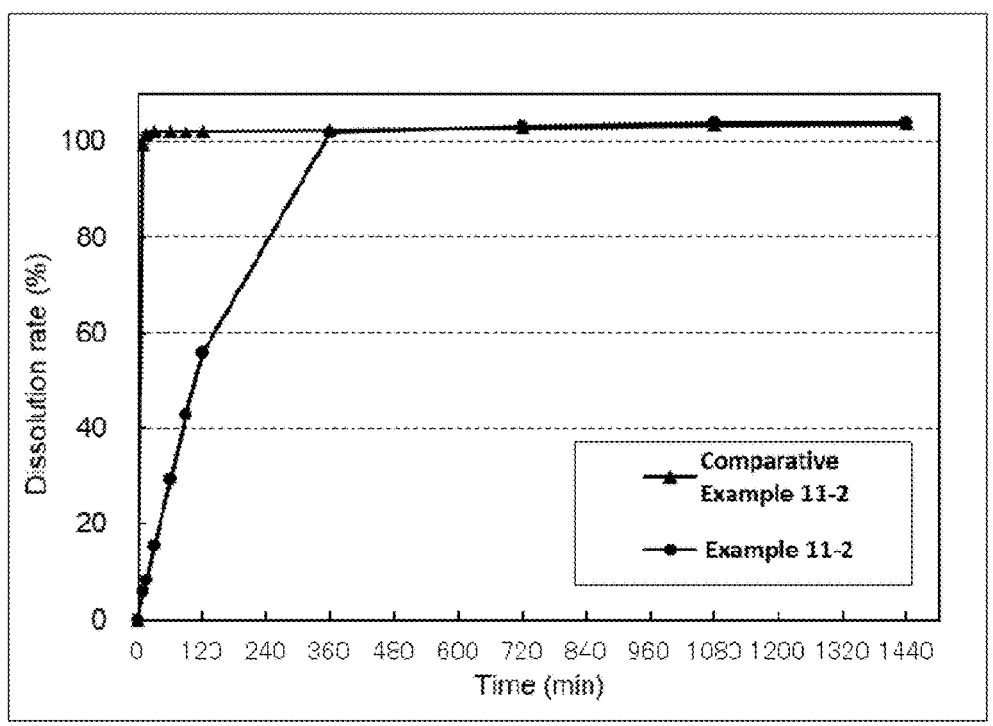
FIG. 14 shows results of dissolution tests of Example 11-2 and Comparative Example 11-2.
Figure 15:
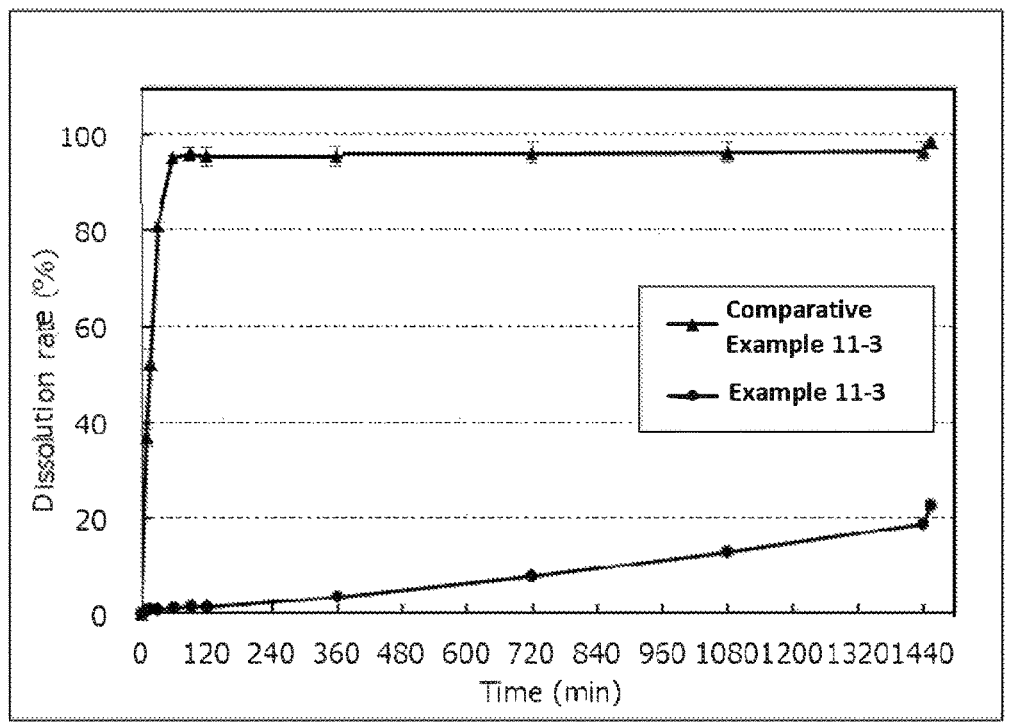
FIG. 15 shows results of dissolution tests of Example 11-3 and Comparative Example 11-3.

Dissolution Test on Coated Component of Interest-Containing Hollow Particles with Different Constituent Active Pharmaceutical Ingredients A dissolution test was conducted using the particles manufactured in Example 11 and Comparative Example 11. The test conditions were the same as Test Example 1. The results are shown in FIGS. 13 to 15. Table 13 shows the coating rate, coating time, and the time that was required for the manufacture of the resulting particles.

Table 13 shows the 50% dissolution times before and after coating for coated component of interest-containing hollow particles using different active pharmaceutical ingredients as constituent active pharmaceutical ingredients. The dissolution time of compound D was extended by a factor of 63 or greater, the dissolution time of compound E was extended by a factor of 21 or greater, and the dissolution time of compound F was extended by a factor of 235 or greater, resulting in an effect of suppressing the release rate.

Test Example 9

Figure 16:
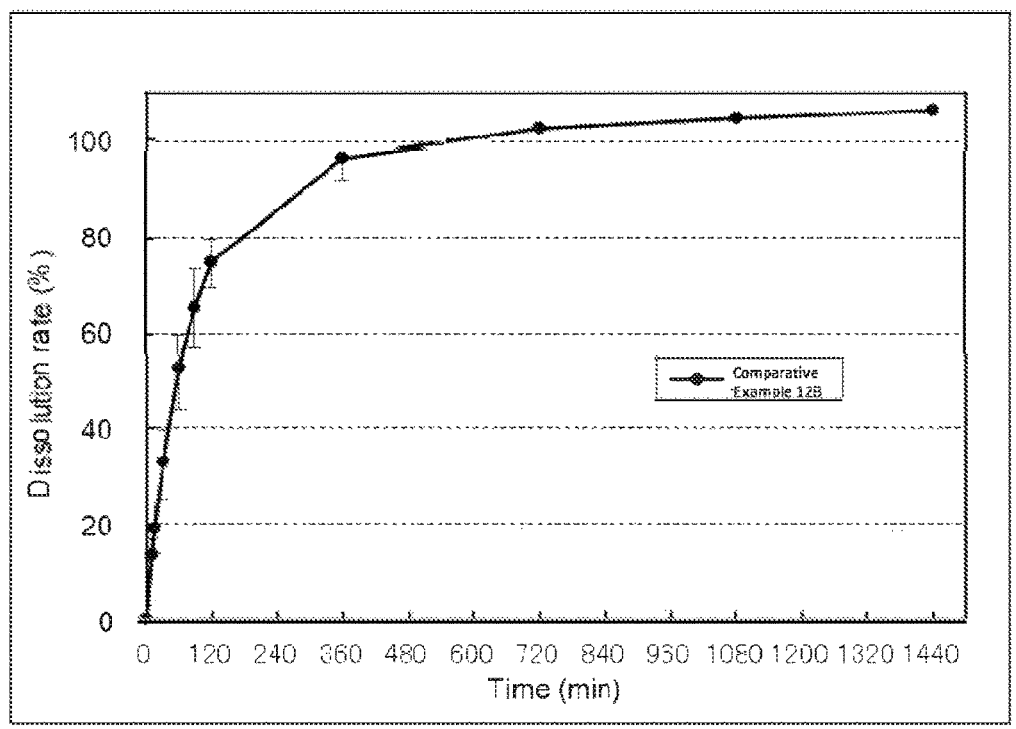
FIG. 16 shows results of dissolution tests of Comparative Example 12B.

Dissolution Test on Component of Interest-Containing Hollow Particles Coated with a Fluidized Bed Granulator A dissolution test was conducted using the particles manufactured in Comparative Example 12B. The test conditions were the same as Test Example 1. The results are shown in FIG. 16. Table 13 shows the coating rate, coating time, and the time that was required for the manufacture of the resulting particles.

Table 13 shows the ratio of 50% dissolution times before and after coating for the coated component of interest-containing hollow particles using coatable microparticles. The dissolution time was 0.55-fold, resulting in hardly any effect of suppressing the release rate.

As disclosed above, the present invention is exemplified by the use of its preferred embodiments. However, it is understood that the scope of the present invention should be interpreted solely based on the Claims. The present application claims priority to Japanese Patent Application No. 2017-254309 (filed on Dec. 28, 2017). The entire content thereof is incorporated herein by reference. It is also understood that any patent, any patent application, and any references cited herein should be incorporated herein by reference in the same manner as the contents are specifically described herein.

INDUSTRIAL APPLICABILITY

The particles of the inventions can be utilized in solid pharmaceutical formulations.

The invention claimed is:

1. A method of manufacturing hollow particles coated with coatable microparticles, comprising:
   mixing the coatable microparticles with an inner core comprising a component of interest and a macromolecule such that a mixture is obtained; and
   performing coating while rolling the mixture and while spraying a solvent that has a property of dissolving the macromolecule, such that hollow particles including the component of interest and coated with the coatable microparticles are obtained,
   wherein the inner core has a shell and a hollow section.

2. The method of claim 1, wherein the coatable microparticles have a D90 value of 100 μm or less.

3. The method of claim 1, wherein the coatable microparticles have a mean particle size of 25 μm or less.

4. The method of claim 1, wherein the coatable microparticles have a D100 value of 150 μm or less.

5. The method of claim 1, wherein the coatable microparticles have a particle size such that all of the coatable microparticles pass through a 100 mesh sieve.

6. The method of claim 1, wherein the coatable microparticles comprise at least one selected from the group consisting of celluloses, stearic acid, stearate, talc, oil and fat, metal oxide, stearyl fumarate salt, and alginic acid.

7. The method of claim 1, wherein the coatable microparticles comprise at least one selected from the group consisting of talc, Red Ferric Oxide, Yellow Ferric Oxide, titanium oxide, sodium stearyl fumarate, and sodium stearate.

8. The method of claim 1, wherein the component of interest is a drug, a cosmetic, an agricultural chemical, a supplement, or a food product.

* * * * *